United States Patent
Winter et al.

(10) Patent No.: US 9,957,498 B2
(45) Date of Patent: May 1, 2018

(54) PHOTOREMOVABLE PROTECTING GROUPS AND USES THEREOF

(71) Applicant: Iowa State University Research Foundation, Inc., Ames, IA (US)

(72) Inventors: Arthur Henry Winter, Ames, IA (US); Christie Lynn Beck, Palm Beach Gardens, FL (US); Kaitlyn Marie Mahoney, Ames, IA (US); Toshia Renee Albright, Ames, IA (US); Pratik Pran Goswami, Ames, IA (US)

(73) Assignee: IOWA STATE UNIVERSITY RESEARCH FOUNDATION, INC., Ames, IA (US)

( * ) Notice: Subject to any disclaimer, the term of this patent is extended or adjusted under 35 U.S.C. 154(b) by 0 days. days.

(21) Appl. No.: 15/016,467

(22) Filed: Feb. 5, 2016

(65) Prior Publication Data

US 2016/0228845 A1 Aug. 11, 2016

Related U.S. Application Data

(60) Provisional application No. 62/112,549, filed on Feb. 5, 2015.

(51) Int. Cl.
  *C07D 209/16* (2006.01)
  *C12N 13/00* (2006.01)
  *C07K 14/805* (2006.01)

(52) U.S. Cl.
  CPC ........... *C12N 13/00* (2013.01); *C07D 209/16* (2013.01); *C07K 14/805* (2013.01); *Y02P 20/55* (2015.11)

(58) Field of Classification Search
  CPC ............................. C12N 13/00; C07D 209/16
  See application file for complete search history.

(56) References Cited

U.S. PATENT DOCUMENTS

2011/0081647 A1* 4/2011 Siddiqi ................. C07H 19/06
                                                                 435/6.1

* cited by examiner

*Primary Examiner* — Shawquia Jackson
(74) *Attorney, Agent, or Firm* — Schwegman Lundberg & Woessner, P.A.

(57) ABSTRACT

The invention relates to a method for photoreleasing a moiety G from a compound of the formula A-G. The methods of the present invention comprise irradiating a composition comprising the compound of the formula A-G at a wavelength of >500 nm, so as to photorelease the moiety G from the moiety A; wherein the moiety A comprises a chromophore and the moiety G comprises an organic compound.

21 Claims, 1 Drawing Sheet

PHOTOREMOVABLE PROTECTING GROUPS AND USES THEREOF

CROSS-REFERENCE TO RELATED APPLICATIONS

This application claims the benefit of priority of U.S. Provisional Appl. Ser. No. 62/112,549, filed Feb. 5, 2015, which is incorporated by reference as if fully set forth herein.

BACKGROUND

Photoremovable protecting groups, sometimes called "photocages" or "phototriggers," are light-sensitive chemical moieties that mask substrates through covalent linkages that render the substrates inert. Upon irradiation, the substrates are released, restoring their reactivity or function. While photocages have important applications in areas such as organic synthesis, photolithography, and light-responsive organic materials, these structures are particularly prized for their ability to trigger biological activity with high spatial and temporal resolution. Examples of such chemical tools include photocaged proteins, nucleotides, ions, neurotransmitters, pharmaceuticals, fluorescent dyes, and small molecules (e.g., caged ATP). These biologically relevant caged molecules and ions can be released from the caging structure within particular biological microenvironments using pulses of focused light. The most popular photocages used in biological studies are the o-nitrobenzyl systems and their derivatives, but other photocages that see significant use include those based on the phenacyl, acridinyl, benzoinyl, coumarinyl, and o-hydroxynaphthyl structures. Unfortunately, a significant limitation of these photocages is that they absorb mostly in the ultraviolet (UV), where the limited penetration of UV light into tissues largely restricts these studies to fixed cells and tissue slices. Furthermore, prolonged exposure of cells or tissues to intense UV light can lead to cellular damage or death. Consequently, new photocaging structures that absorb visible light are needed.

SUMMARY

Embodiments of the present invention relate to photoremovable groups that are photoremovable at wavelengths of light greater than 500 nm.

In one embodiment, the invention relates to a method for photoreleasing a moiety G, or a fragment thereof, from a compound of the formula A-G comprising: irradiating a composition comprising the compound of the formula A-G at a wavelength of >500 nm, so as to photorelease the moiety G, or a fragment thereof, from the moiety A; wherein the moiety A comprises a chromophore and the moiety G, or fragment thereof, comprises an organic compound.

BRIEF DESCRIPTION OF THE FIGURES

The drawings illustrate generally, by way of example, but not by way of limitation, various embodiments discussed in the present document.

DETAILED DESCRIPTION OF THE INVENTION

Figure 1:
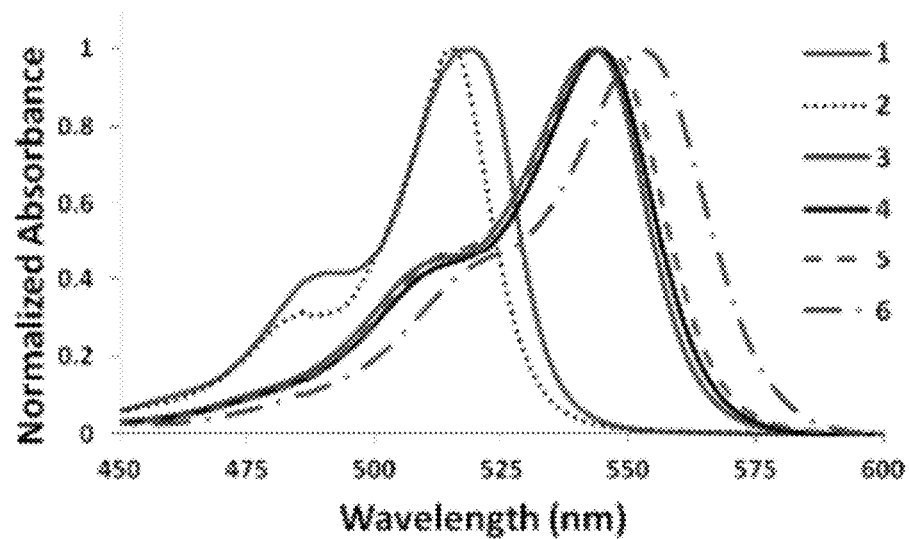
FIG. 1 is a plot of normalized absorbance as a function of wavelength for compounds 1-6 described herein.
Figure 2:
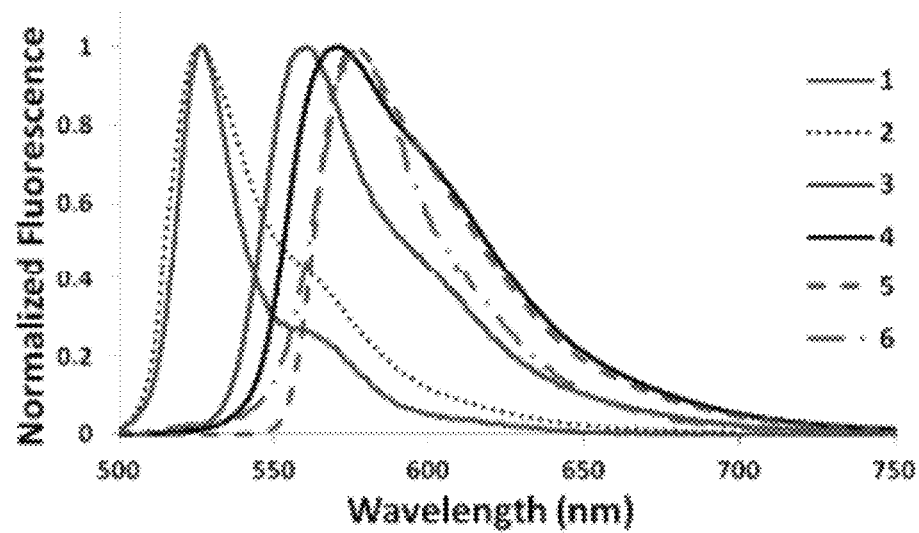
FIG. 2 is a plot of normalized fluorescence as a function of wavelength for compounds 1-6 described herein.

Reference will now be made in detail to embodiments of the present invention, examples of which are illustrated in part in the accompanying drawings. While the disclosed embodiments of the present invention will be described in conjunction with the enumerated claims, it will be understood that the exemplified embodiments of the present invention are not intended to limit the claims to the disclosed embodiments.

Values expressed in a range format should be interpreted in a flexible manner to include not only the numerical values explicitly recited as the limits of the range, but also to include all the individual numerical values or sub-ranges encompassed within that range as if each numerical value and sub-range were explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

In the methods described herein, the steps can be carried out in any order without departing from the principles of the invention, except when a temporal or operational sequence is explicitly recited. Furthermore, specified steps can be carried out concurrently unless explicit claim language recites that they be carried out separately. For example, a claimed step of doing X and a claimed step of doing Y can be conducted simultaneously within a single operation, and the resulting process will fall within the literal scope of the claimed process.

The term "about" as used herein can allow for a degree of variability in a value or range, for example, within 10%, within 5%, or within 1% of a stated value or of a stated limit of a range.

The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more.

The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those of ordinary skill in the art, and that such modifications and variations are considered to be within the scope of this invention as defined by the appended claims.

Overview

Embodiments of the present invention relate to a method for photoreleasing a moiety G, or fragment thereof, from a compound of the formula A-G. The method comprises irradiating a composition (e.g., within a cell comprising a compound of the formula A-G; or a solution of a compound of the formula A-G in any suitable organic, preferably polar, solvent, such as acetonitrile or an alkanol including methanol, ethanol, and the like; an aqueous solvent; or combinations of an organic solvent and an aqueous solvent) comprising the compound of the formula A-G at a wavelength of >500 nm, so as to photorelease the moiety G, or fragment thereof, from the moiety A; wherein the moiety A comprises a chromophore and the moiety G, or fragment thereof, comprises an organic compound (e.g., at least one of a protein, an oligopeptide, an amino acid, an oligonucleotide, an ion, a small molecule, and the like). In some embodiments, the compound of the formula A-G has a wavelength absorption maximum, $\lambda_{max}$, between about 510 nm to about 1000 nm (e.g., between about 510 nm to about 550 nm; about 520 nm to about 650 nm; about 525 nm to about 675 nm; about 550 nm to about 650 nm; about 600 nm to about 700 nm; about 600 nm to about 800 nm; about 700 nm to about 900 nm; or about 600 nm to about 1000 nm).

Independent of a $\lambda_{max}$ between about 510 nm to about 1000 nm or in addition to having a $\lambda_{max}$ between about 510 nm to about 1000 nm, the compound of the formula A-G can have an extinction coefficient measured at the compound A-G $\lambda_{max}$, of from about $4.0 \times 10^4$ $M^{-1}$ $cm^{-1}$ to about $8.0 \times 10^4$ $M^{-1}$ $cm^{-1}$ (e.g., from about $4.5 \times 10^4$ $M^{-1}$ $cm^{-1}$ to about $7.5 \times 10^4$ $M^{-1}$ $cm^{-1}$; about $5.0 \times 10^4$ $M^{-1}$ $cm^{-1}$ to about $8.0 \times 10^4$ $M^{-1}$ $cm^{-1}$; about $5.5 \times 10^4$ $M^{-1}$ $cm^{-1}$ to about $7.5 \times 10^4$ $M^{-1}$ $cm^{-1}$; or about $6.0 \times 10^4$ $M^{-1}$ $cm^{-1}$ to about $8.0 \times 10^4$ $M^{-1}$ $cm^{-1}$).

The Moiety "A"

In some embodiments, the chromophore comprised in the moiety A comprises a boron-dipyrromethane (BODIPY) chromophore. In some embodiments, the moiety A comprises a BODIPY chromophore of the formula I:

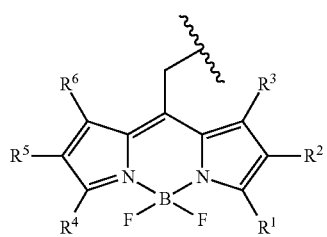

I wherein:
the wavy line represents the attachment point of the moiety A to the moiety G; $R^1$, $R^2$, $R^3$, $R^4$, $R^5$, and $R^6$ are each, independently, hydrogen, halogen, optionally substituted $C_1$-$C_6$-alkyl, optionally substituted $C_2$-$C_6$-alkenyl or ($C_6$-$C_{14}$-aryl)-($C_2$-$C_6$-alkenyl-), wherein the ($C_6$-$C_{14}$-aryl)-($C_2$-$C_6$-alkenyl-) is optionally substituted on the $C_2$-$C_6$-alkenyl or the $C_6$-$C_{14}$-aryl. In some embodiments, $R^1$, $R^2$, $R^3$, $R^4$, $R^5$, and $R^6$ are each, independently, hydrogen, halogen, optionally substituted $C_1$-$C_6$-alkyl, optionally substituted $C_2$-$C_6$-alkenyl, ($C_6$-$C_{14}$-aryl)-($C_2$-$C_6$-alkenyl-), wherein the ($C_6$-$C_{14}$-aryl)-($C_2$-$C_6$-alkenyl-) is optionally substituted on the $C_2$-$C_6$-alkenyl or the $C_6$-$C_{14}$-aryl or optionally substituted ($C_2$-$C_8$-heterocyclyl-).

Independent of the BODIPY chromophore or in addition to the BODIPY chromophore, the moiety G comprises any molecule that can be photoreleasably linked by any suitable means to the moiety A. Compounds of the formula A-G comprising the BODIPY chromophore have significant advantages over known photoremovable groups at least because: (i) they can be removed by irradiating at a wavelength of >500 nm; (ii) ease of their synthesis; (iii) the BODIPY chromophore is biocompatible (Choyke et al., Mol. Imaging 8: 1536 (2009)); and the compounds A-G comprising the BODIPY chromophore have excellent optical properties (e.g., high extinction coefficients $4.0 \times 10^4$ $M^{-1}$ $cm^{-1}$ to about $8.0 \times 10^4$ $M^{-1}$ $cm^{-1}$). In sum, the BODIPY chromophore can replace known photoremovable groups, such as the o-nitrobenzyl photoremovable groups, and can be used as protecting groups for any moiety G for which known photoremovable groups have previously been used to protect including nucleotides, peptides, proteins, carboxylates (e.g., acetic acid; gamma aminobutyric acid; N-methyl-D-aspartate; arachidonic acid; and lipids); amines, amides, alcohols, phenols, phosphates, ions (e.g., $Ca^{2+}$); and fluorophores/dyes (e.g., 7-hydroxycoumarins, pyrenes; and rhodamines). See Petr Klán et al., Chem. Rev. 113: 119-191 (2013); and Dynamic Studies in Biology 5-20 (Maurice Goeldner and Richard Givens eds., Wiley VCH Verlag GmbH & Co. KGaA 2005), both of which are incorporated by reference as if fully set forth herein.

As used herein, the term "$C_{1-6}$-alkyl" refers to monovalent saturated aliphatic hydrocarbyl groups having from 1 to 6 carbon atoms. This term includes, but is not limited to, linear and branched hydrocarbyl groups such as methyl ($CH_3$—), ethyl ($CH_3CH_2$—), n-propyl ($CH_3CH_2CH_2$—), isopropyl (($CH_3$)$_2$CH—), n-butyl ($CH_3CH_2CH_2CH_2$—), isobutyl (($CH_3$)$_2$CHCH$_2$—), sec-butyl (($CH_3$)($CH_3CH_2$)CH—), t-butyl (($CH_3$)$_3$C—), n-pentyl ($CH_3CH_2CH_2CH_2CH_2$—), and neopentyl (($CH_3$)$_3$CCH$_2$—). The term $C_{1-6}$-alkyl also includes cycloalkyl groups including, but not limited to, cyclopropyl, cyclobutyl, cyclopentyl, and cyclohexyl.

The term "$C_1$-$C_{20}$-alkylenyl" as used herein refers to straight chain and branched, saturated divalent groups having from 1 to 20 carbon atoms, 10 to 20 carbon atoms, 12 to 18 carbon atoms, 1 to about 20 carbon atoms, 1 to 10 carbons, 1 to 8 carbon atoms, 1 to 6 carbon atoms or 2 to 4 carbon atoms. Examples of straight chain $C_1$-$C_{20}$-alkylenyl groups include those with from 1 to 6 carbon atoms such as —$CH_2$—, —$CH_2CH_2$—, —$CH_2CH_2CH_2$—, —$CH_2CH_2CH_2CH_2$—, and —$CH_2CH_2CH_2CH_2CH_2$—. Examples of branched ($C_1$-$C_{20}$)-alkylenyl groups include —CH($CH_3$)$CH_2$— and —$CH_2$CH($CH_3$)$CH_2$—.

As used herein, the term "$C_{2-6}$-alkenyl" refers to monovalent and divalent unsaturated hydrocarbyl groups having from 2 to 6 carbon atoms. This term includes, but is not limited to, linear and branched hydrocarbyl groups such as vinyl ($CH_2$=CH—), propenyl ($CH_2$=$CH_2CH_2$—), isopropenyl (($CH_3$)($CH_2$)C—), —CH=CH—, —CH=CH—$CH_2$—, —CH=CH—CH=CH—, and the like. The term $C_{2-6}$-alkenyl also includes cycloalkenyl groups including, but not limited to, cyclopentenyl and cyclohexenyl.

As used herein, the term "$C_6$-$C_{14}$-aryl" refers to cyclic aromatic hydrocarbons having from 6 to 14 carbon atoms (e.g., 6 to 12 carbon atoms or 6 to 10 carbon atoms). Such aryl groups may be substituted or unsubstituted. Aryl groups include, but are not limited to, phenyl, biphenyl, fluorenyl, phenanthrenyl, and naphthyl groups.

As used herein, the term "$C_2$-$C_8$-heterocycyclyl" refers to cyclic aromatic or non-aromatic hydrocarbons having from 2 to 8 carbon atoms (e.g., 3 to 5 carbon atoms) and one or more heteroatoms such as nitrogen, oxygen or sulfur. Such heterocyclyl groups may be monocyclic or fused by cyclic and can be substituted or unsubstituted. Heterocyclyl groups include, but are not limited to, pyridinyl, pyrimidinyl, pyrazinyl, triazinyl, quinolinyl, quinazolinyl, quinoxalinyl, furanyl, thiophenyl, pyrrolyl, pyrazolyl, imidazolyl, oxazolyl, thiazolyl, isoxazolyl, isothiazolyl, oxadiazolyl, thiadiazolyl, triazolyl, benzimidazolyl, benzoxazolyl, benzthiazolyl, benzisoxazolyl, benzisothiazolyl, piperidynyl, piperazinyl, morpholinyl, pyrrolidinyl, tetrahydrofuranyl, and the like.

"Substituted" as used throughout the specification refers broadly to replacement of one or more of the hydrogen atoms of a group (e.g., $C_{1-6}$-alkyl, $C_{2-6}$-alkenyl, $C_6$-$C_{14}$-aryl, and $C_2$-$C_8$-heterocyclyl) with substituents known to those skilled in the art and resulting in a stable compound as described herein. Examples of suitable substituents include, but are not limited to, alkyl (e.g., $C_{1-6}$-alkyl), alkenyl (e.g., $C_{2-6}$-alkenyl), aryl (e.g., $C_6$-$C_{14}$-aryl), alkaryl (e.g., $C_{1-6}$-alkyl-$C_6$-$C_{14}$-aryl), hydroxy, alkoxy (e.g., $C_{1-6}$-alkyl-O—), aryloxy (e.g., $C_6$-$C_{14}$-aryl-O—), carboxy (i.e., $CO_2H$), alkylcarboxy (e.g., $C_{1-6}$-alkyl-C(O)O—), arylcarboxy (e.g., $C_6$-$C_{14}$-aryl-C(O)O—), cyano, cyanate ester (i.e., an —OCN group), silyl, siloxyl, phosphine, halogen (e.g., F, Cl, Br, and I), nitro, and $C_2$-$C_8$-heterocyclyl-. Other suitable substituents include —N($R^8$)$_2$, wherein each $R^8$ is hydrogen, alkyl (e.g., $C_{1-6}$-alkyl), aryl (e.g., $C_6$-$C_{14}$-aryl) or alkaryl (e.g., $C_{1-6}$-alkyl-$C_6$-$C_{14}$-aryl), wherein each alkyl, aryl or alkaryl can be substituted; and —[O—$R^9$—]$_p$O—$R^{10}$, wherein $R^9$ is alkylenyl (e.g., $C_1$-$C_{20}$-alkylenyl) or cycloalkylenyl (e.g., ($C_3$-$C_{20}$)-cycloalkylenyl), $R^{10}$ is alkyl (e.g., $C_{1-6}$-alkyl), and p is an integer from 1 to about 10 (e.g., an integer from 1 to 5, 2 to 8, 2 to 5 or 2 to 4).

In some embodiments, $R^1$ and $R^4$ in the moiety A are each, independently, an optionally substituted $C_1$-$C_6$-alkyl. In some embodiments, $R^1$ and $R^4$ are each methyl.

In some embodiments, $R^3$ and $R^6$ in the moiety A, are each, independently, an optionally substituted $C_1$-$C_6$-alkyl. In some embodiments, $R^3$ and $R^6$ are each methyl. In other embodiments, $R^1$, $R^3$, $R^4$, and $R^6$ in the moiety A, are each, independently, an optionally substituted $C_1$-$C_6$-alkyl. For example, $R^1$, $R^3$, $R^4$, and $R^6$ in the moiety A can each be methyl.

In some embodiments, $R^2$ and $R^5$ in the moiety A, are each, independently, an optionally substituted $C_1$-$C_6$-alkyl. In some embodiments, $R^2$ and $R^5$ are each, independently, methyl or ethyl. In other embodiments, $R^1$, $R^2$, $R^3$, $R^4$, $R^5$, and $R^6$ in the moiety A, are each, independently, an optionally substituted $C_1$-$C_6$-alkyl. For example, $R^1$, $R^3$, $R^4$, and $R^6$ in the moiety A are each methyl and $R^2$ and $R^5$ are each, independently, methyl or ethyl; or $R^1$, $R^3$, $R^4$, and $R^6$ in the moiety A are each methyl and $R^2$ and $R^5$ are each ethyl.

In still other embodiments, $R^2$ and $R^5$ are each, independently, halogen. In some embodiments, $R^2$ and $R^5$ are each, independently, fluorine, chlorine, bromine, iodine or combinations thereof. In other embodiments, $R^2$ and $R^5$ are each, independently, chlorine, bromine, iodine or combinations thereof. In still other embodiments, $R^2$ and $R^5$ are each chlorine, bromine or iodine. In yet other embodiments, $R^2$ and $R^5$ are each, independently, halogen and $R^1$, $R^3$, $R^4$, and $R^6$ are each, independently, an optionally substituted $C_1$-$C_6$-alkyl. In still other embodiments, $R^2$ and $R^5$ are each, independently, halogen and $R^1$, $R^3$, $R^4$, and $R^6$ are each methyl. In yet other embodiments, $R^2$ and $R^5$ are each, independently, chlorine, bromine or iodine and $R^1$, $R^3$, $R^4$, and $R^6$ are each methyl.

In other embodiments, $R^1$ and $R^4$ are each, independently, ($C_6$-$C_{14}$-aryl)-($C_2$-$C_6$-alkenyl-), wherein the ($C_6$-$C_{14}$-aryl)-($C_2$-$C_6$-alkenyl-) is optionally substituted on the $C_2$-$C_6$-alkenyl or the $C_6$-$C_{14}$-aryl; that is, the ($C_6$-$C_{14}$-aryl)-($C_2$-$C_6$-alkenyl-) is optionally substituted on the $C_2$-$C_6$-alkenyl, the $C_6$-$C_{14}$-aryl or both. In some embodiments, $R^1$ and $R^4$ are each, independently, ($C_6$-$C_{10}$-aryl)-($C_2$-$C_4$-alkenyl-), wherein the ($C_6$-$C_{10}$-aryl)-($C_2$-$C_4$-alkenyl-) is optionally substituted on the $C_2$-$C_4$-alkenyl or the $C_6$-$C_{10}$-aryl; that is, the ($C_6$-$C_{10}$-aryl)$C_2$-$C_4$-alkenyl-) is optionally substituted on the $C_2$-$C_4$-alkenyl, the $C_6$-$C_{10}$-aryl or both. In other embodiments, $R^1$ and $R^4$ are each —CH═CH—$C_6$-$C_{10}$-aryl, wherein the $C_6$-$C_{10}$-aryl is optionally substituted. In still other embodiments, $R^1$ and $R^4$ are each —CH═CH-phenyl, wherein the phenyl is optionally substituted.

In other embodiments, $R^1$ and $R^4$ are each, independently, ($C_6$-$C_{14}$-aryl)-($C_2$-$C_6$-alkenyl-), wherein the ($C_6$-$C_{14}$-aryl)-($C_2$-$C_6$-alkenyl-) is optionally substituted on the $C_2$-$C_6$-alkenyl or the $C_6$-$C_{14}$-aryl; that is, the ($C_6$-$C_{14}$-aryl)-($C_2$-$C_6$-alkenyl-) is optionally substituted on the $C_2$-$C_6$-alkenyl, the $C_6$-$C_{14}$-aryl or both; and $R^3$ and $R^6$ are each, independently, an optionally substituted $C_1$-$C_6$-alkyl. In some embodiments, $R^1$ and $R^4$ are each, independently, ($C_6$-$C_{10}$-aryl)-($C_2$-$C_4$-alkenyl-), wherein the ($C_6$-$C_{10}$-aryl)-($C_2$-$C_4$-alkenyl-) is optionally substituted on the $C_7$-$C_4$-alkenyl or the $C_6$-$C_{10}$-aryl; that is, the ($C_6$-$C_{10}$-aryl)-($C_2$-$C_4$-alkenyl-) is optionally substituted on the $C_2$-$C_4$-alkenyl, the $C_6$-$C_{10}$-aryl or both; and $R^3$ and $R^6$ are each, independently, an optionally substituted $C_1$-$C_6$-alkyl. In other embodiments, $R^1$ and $R^4$ are each —CH═CH—$C_6$-$C_{10}$-aryl, wherein the $C_6$-$C_{10}$-aryl is optionally substituted; and $R^3$ and $R^6$ are each, independently, an optionally substituted $C_1$-$C_6$-alkyl. In still other embodiments, $R^1$ and $R^4$ are each —CH═CH-phenyl, wherein the phenyl is optionally substituted; and $R^3$ and $R^6$ are each, independently, an optionally substituted $C_1$-$C_6$-alkyl. In still other embodiments, $R^1$ and $R^4$ are each —CH═CH-phenyl, wherein the phenyl is optionally substituted; and $R^3$ and $R^4$ are each methyl.

In other embodiments, $R^1$ and $R^4$ are each, independently, ($C_6$-$C_{14}$-aryl)-($C_2$-$C_6$-alkenyl-), wherein the ($C_6$-$C_{14}$-aryl)-($C_2$-$C_6$-alkenyl-) is optionally substituted on the $C_2$-$C_6$-alkenyl or the $C_6$-$C_{14}$-aryl; that is, the ($C_6$-$C_{14}$-aryl)-($C_2$-$C_6$-alkenyl-) is optionally substituted on the $C_2$-$C_6$-alkenyl, the $C_6$-$C_{14}$-aryl or both; $R^3$ and $R^6$ are each, independently, an optionally substituted $C_1$-$C_6$-alkyl; and $R^2$ and $R^5$ are each hydrogen. In some embodiments, $R^1$ and $R^4$ are each, independently, ($C_6$-$C_{10}$-aryl)-($C_2$-$C_4$-alkenyl-), wherein the $C_6$-$C_{10}$-aryl)-($C_2$-$C_4$-alkenyl-) is optionally substituted on the $C_2$-$C_4$-alkenyl or the $C_6$-$C_{10}$-aryl; that is, the ($C_6$-$C_{10}$-aryl)-($C_2$-$C_4$-alkenyl-) is optionally substituted on the $C_2$-$C_4$-alkenyl, the $C_6$-$C_{10}$-aryl or both; $R^3$ and $R^6$ are each, independently, an optionally substituted $C_1$-$C_6$-alkyl; and $R^2$ and $R^5$ are each hydrogen. In other embodiments, $R^1$ and $R^4$ are each —CH═CH—$C_6$-$C_{10}$-aryl, wherein the $C_6$-$C_{10}$-aryl is optionally substituted; $R^3$ and $R^6$ are each, independently, an optionally substituted $C_1$-$C_6$-alkyl; and $R^2$ and $R^5$ are each hydrogen. In still other embodiments, $R^1$ and $R^4$ are each —CH═CH-phenyl, wherein the phenyl is optionally substituted; $R^3$ and $R^6$ are each, independently, an optionally substituted $C_1$-$C_6$-alkyl; and $R^2$ and $R^5$ are each hydrogen. In still other embodiments, $R^1$ and $R^4$ are each —CH═CH-phenyl, wherein the phenyl is optionally substituted; $R^3$ and $R^6$ are each methyl; and $R^2$ and $R^5$ are each hydrogen.

In other embodiments, one of $R^1$ and $R^4$ is an optionally substituted $C_1$-$C_6$-alkyl; and one of $R^1$ and $R^4$ is ($C_6$-$C_{14}$-aryl)-($C_2$-$C_6$-alkenyl-), wherein the ($C_6$-$C_{14}$-aryl)-($C_2$-$C_6$-alkenyl-) is optionally substituted on the $C_2$-$C_6$-alkenyl or the $C_6$-$C_{14}$-aryl; that is, the ($C_6$-$C_{14}$-aryl)-($C_2$-$C_6$-alkenyl-) is optionally substituted on the $C_2$-$C_6$-alkenyl, the $C_6$-$C_{14}$-aryl or both. In some embodiments, one of $R^1$ and $R^4$ is an optionally substituted $C_1$-$C_6$-alkyl; and one of $R^1$ and $R^4$ is ($C_6$-$C_{10}$-aryl)-($C_2$-$C_4$-alkenyl-), wherein the $C_6$-$C_{10}$-aryl)-($C_2$-$C_4$-alkenyl-) is optionally substituted on the $C_2$-$C_4$-alkenyl or the $C_6$-$C_{10}$-aryl; that is, the ($C_6$-$C_{10}$-aryl)-($C_2$-$C_4$-alkenyl-) is optionally substituted on the $C_2$-$C_4$-alkenyl, the $C_6$-$C_{10}$-aryl or both. In other embodiments, one of $R^1$ and $R^4$ is an optionally substituted $C_1$-$C_6$-alkyl; and one of $R^1$ and $R^4$ is —CH═CH—$C_6$-$C_{10}$-aryl, wherein the $C_6$-$C_{10}$-aryl is optionally substituted. In still other embodiments, one of $R^1$ and $R^4$ is an optionally substituted $C_1$-$C_6$-alkyl; and one of $R^1$ and $R^4$ is —CH═CH-phenyl, wherein the phenyl is optionally substituted. In still other embodiments, one of $R^1$ and $R^4$ is methyl; and one of $R^1$ and $R^4$ is —CH═CH-phenyl, wherein the phenyl is optionally substituted.

In some embodiments, the moiety A is a moiety of the formula:

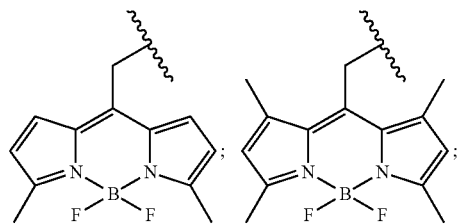

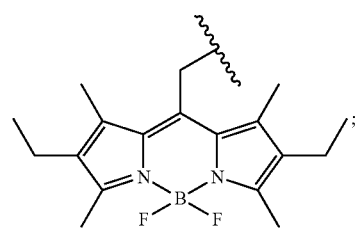

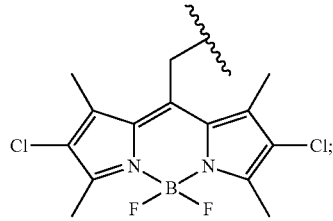

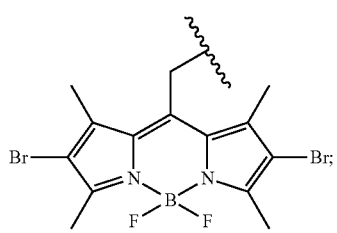

-continued

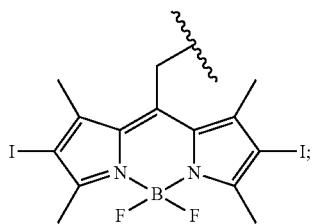

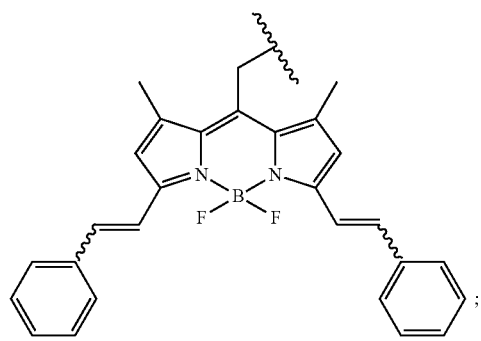

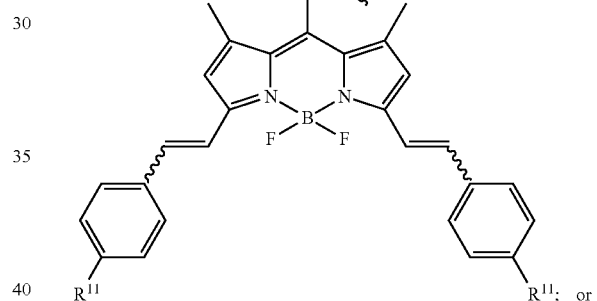

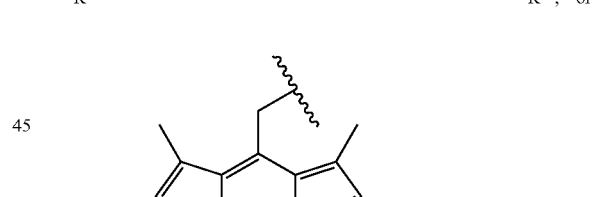

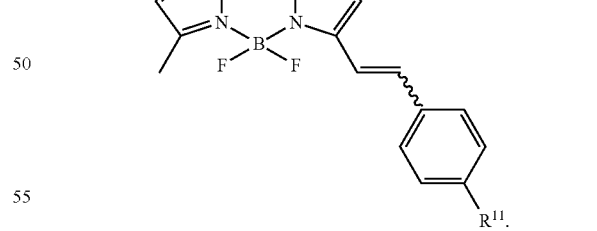

wherein $R^{11}$ is H; $C_{1-6}$-alkyl-O— (e.g., —OCH$_3$); —N($R^8$)$_2$, wherein each $R^8$ is hydrogen, alkyl (e.g., $C_{1-6}$-alkyl), aryl (e.g., $C_6$-$C_{14}$-aryl) or alkaryl (e.g., $C_{1-6}$-alkyl-$C_6$-$C_{14}$-aryl) (e.g., —N(CH$_3$)$_2$), or —O—$C_{1-6}$-alkyl-O—$C_{1-6}$-alkyl (e.g., (OCH$_2$CH$_2$)$_3$OCH$_3$).

In still other embodiments, the moiety A is a moiety of the formula:

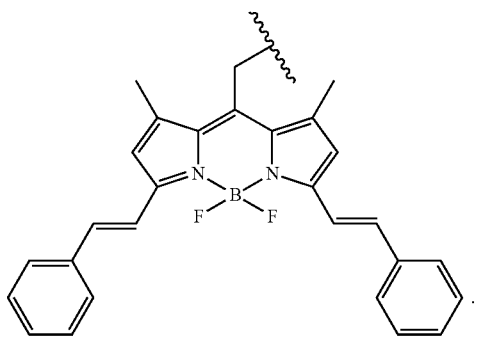

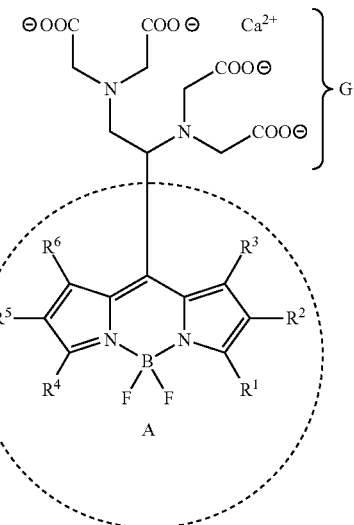

wherein the moiety A is depicted within the broken circle; and $R^1$, $R^2$, $R^3$, $R^4$, $R^5$, and $R^6$ are each, independently, hydrogen, halogen, optionally substituted $C_1$-$C_6$-alkyl, optionally substituted $C_2$-$C_6$-alkenyl or $(C_6$-$C_{14}$-aryl$)$-$(C_2$-$C_6$-alkenyl-$)$, wherein the $(C_6$-$C_{14}$-aryl$)$-$(C_2$-$C_6$-alkenyl-$)$ is optionally substituted on the $C_2$-$C_6$-alkenyl or the $C_6$-$C_{14}$-aryl. In this specific, non-limiting example, the moiety that is photoreleased is a fragment G' of the moiety G as show in Scheme I. In this instance, G' also includes the $Ca^{2+}$ ion.

While not wishing to be bound by any specific theory, it is believed that irradiating a composition comprising the compounds of the formula A-G described herein at a wavelength of >500 nm excites such compounds to their excited singlet state. It is believed that these compounds have excited singlet states with considerable diradical character. The excited singlet state undergoes heterolysis to generate an anion and a carbocation (carbocation not shown in Scheme I) that may be described as having ion diradical character rather than a closed-shell carbocation.

Scheme I

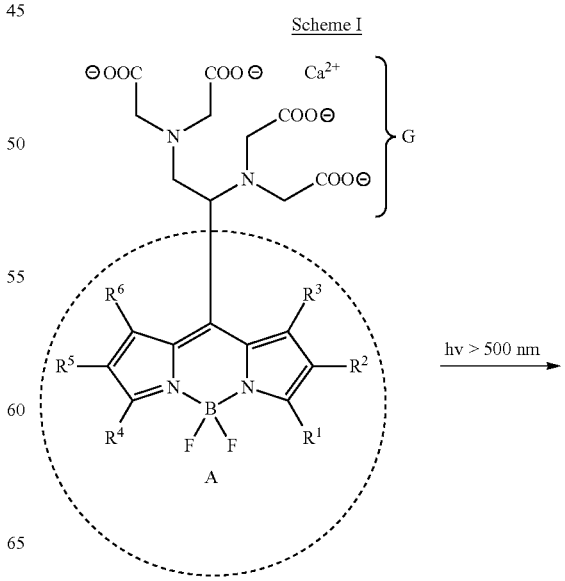

hv > 500 nm

The Moiety "G"

The moiety G in compounds of the formula A-G can be any organic or inorganic compound that can be photoreleasably linked directly or indirectly by any suitable means (e.g., covalently via ether, amine, ester, amide or carbamate linkages, or the like) to the moiety A. The various compounds, organic and inorganic, that are contemplated herein for the moiety G include, but are not limited to, the "caged" or "masked" portion of the compounds described in Petr Klán et al., Chem. Rev. 113: 119-191 (2013); Dynamic Studies in Biology 5-20 (Maurice Goeldner and Richard Givens eds., Wiley VCH Verlag GmbH & Co. KGaA 2005); and Haitao Yu et al., Chem. Soc. Rev. 39: 465-473 (2010); all of which are incorporated by reference as if fully set forth herein.

When the moiety G, or fragment thereof, is photoreleased via the various embodiments of the methods described herein, the moiety G can be in an ionic form, e.g., a carboxylate ($RCOO^-$); an $RO^-$ anion; an $RS^-$ anion; an $ROP(O)_2O^-$ anion; an $RP(O)_2O^-$ anion; an $R_2N^-$ anion; and the like, wherein R is an optionally substituted $C_1$-$C_6$-alkyl, optionally substituted $C_2$-$C_6$-alkenyl, optionally substituted $C_6$-$C_{14}$-aryl, $(C_6$-$C_{14}$-aryl$)$-$(C_2$-$C_6$-alkenyl-$)$, wherein the $(C_6$-$C_{14}$-aryl$)$-$(C_2$-$C_6$-alkenyl-$)$ is optionally substituted on the $C_2$-$C_6$-alkenyl or the $C_6$-$C_{14}$-aryl or optionally: substituted $(C_2$-$C_8$-heterocyclyl-$)$.

Examples of the moiety G include, but are not limited to, at least one of a protein, an oligopeptide, an amino acid, an oligonucleotide, an ion, and a small molecule. As used herein, the term "oligopeptide" refers to a molecule comprising 2 to 100 amino acid residues, e.g., 2 to 20 amino acid residues. As used herein, the term "oligonucleotide" refers to single-stranded nucleotide chain (as an oligodeoxynucleotide or oligoribonucleotide) comprising 2 to 100 nucleotides, e.g., 2 to 20 nucleotides.

Examples of proteins that may be comprised in the moiety G include, but are not limited to, caspases (e.g., caspase-3), phosphatases (e.g., protein tyrosine phosphatase), cholinesterases (e.g., acetylcholinesterase and butyrylcholinesterase), esterases, transferases, restriction endonucleases (e.g. BamH1), hemoglobin, and the like.

Examples of ions include, but are not limited to, caged ions where the ion is caged within a chelating moiety, such as ethylenediamine tetraacetic acid (EDTA) and ethylene glycol tetraacetic acid (EGTA). Suitable ions include but are not limited to $Ca^{2+}$, $Mg^{2+}$, and the like. A non-limiting example of a compound of the formula A-G comprising a moiety G comprising a caged $Ca^{2+}$ is:

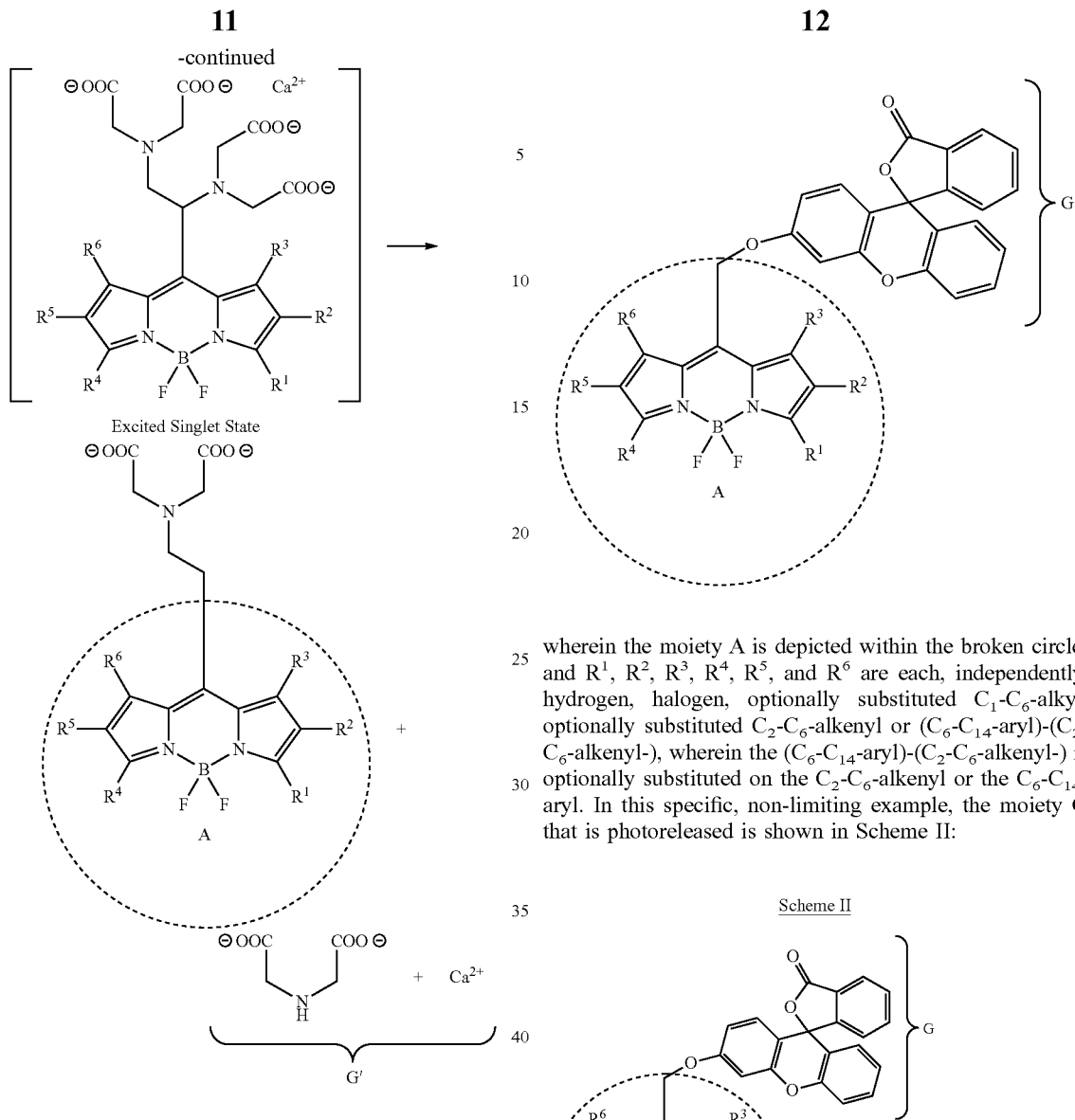

wherein the moiety A is depicted within the broken circle; and $R^1$, $R^2$, $R^3$, $R^4$, $R^5$, and $R^6$ are each, independently, hydrogen, halogen, optionally substituted $C_1$-$C_6$-alkyl, optionally substituted $C_2$-$C_6$-alkenyl or ($C_6$-$C_{14}$-aryl)-($C_2$-$C_6$-alkenyl-), wherein the ($C_6$-$C_{14}$-aryl)-($C_2$-$C_6$-alkenyl-) is optionally substituted on the $C_2$-$C_6$-alkenyl or the $C_6$-$C_{14}$-aryl. In this specific, non-limiting example, the moiety G that is photoreleased is shown in Scheme II:

Scheme II

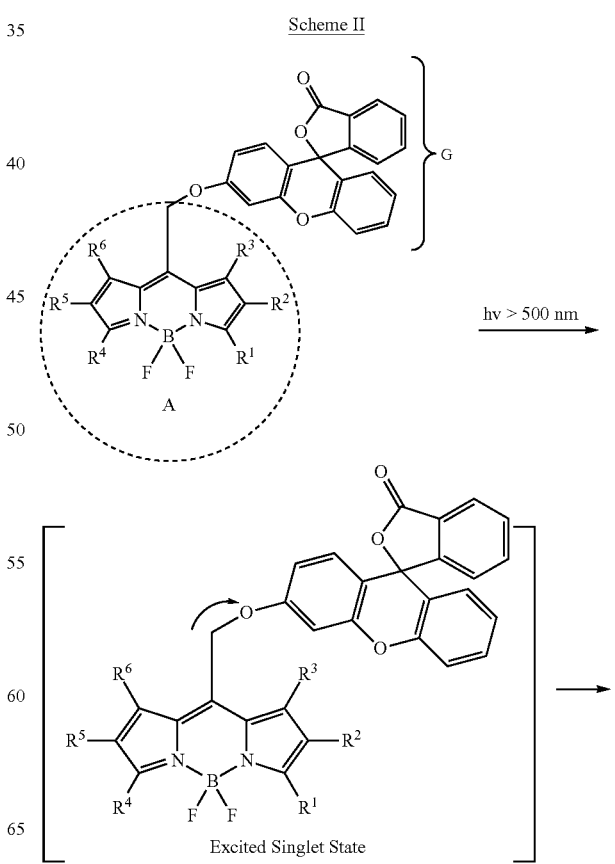

As used herein, the term "small molecule" comprised in the moiety G includes, but is not limited to a molecule having a molecular weight of less than 1000 g/mol. Examples of small molecules include, but are not limited to dyes, fragrances, nucleosides (e.g., adenosine, guanosine, uridine, cytidine, deoxyadenosine, deoxyguanosine, thymidine, deoxyuridine, and deoxycytidine), nucleotides (e.g., adenosine monophosphate, guanosine monophosphate, uridine monophosphate, cytidine monophosphate, deoxyadenosine monophospate, deoxyguanosine monophosphate, thymidine monophosphate, deoxyuridine monophosphate, and deoxycytidine monophosphate), neurotransmitters, pharmaceutical agents, and compounds involved in local immune responses, such as histamines. Nucleoside and nucleotide di- and triphosphates are also contemplated herein, including, but not limited to adenosine triphosphate (ATP) and guanosine triphosphate (GTP).

As used herein, the term "dye" includes any suitable dye including rhodamine-based dyes, fluorescein-based dyes, xanthene-based dyes, coumarins, cyanines, and boron dipyromethanes (BODIPYs). A non-limiting example of a compound of the formula A-G comprising a xanthene-based dye is:

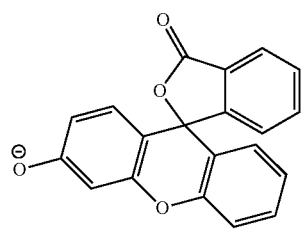

As used herein, the term fragrance includes, but is not limited to, terpene fragrances (e.g., damascone, geraniol, nerol, citronellol, linalool, and nerolidol or derivatives thereof), cyclic terpene fragrances (e.g., terpineol or derivatives thereof), aromatic fragrances (e.g., eugenol, vannilin, benzaldehyde, cinnamaldehyde, ethyl maltol, and thymol or derivatives thereof), and the like. In a specific, non-limiting example, the moiety G that is photoreleased is a damascone derivate, as shown in Scheme III:

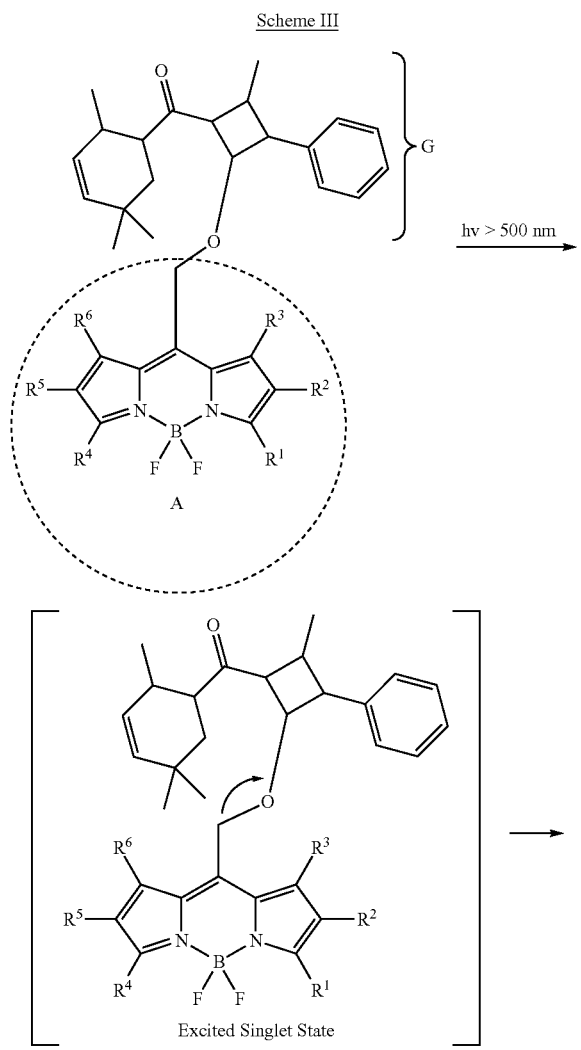

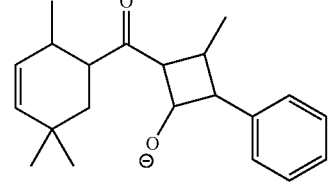

wherein the moiety A is depicted within the broken circle; and $R^1$, $R^2$, $R^3$, $R^4$, $R^5$, and $R^6$ are each, independently, hydrogen, halogen, optionally substituted $C_1$-$C_6$-alkyl, optionally substituted $C_2$-$C_6$-alkenyl or ($C_6$-$C_{14}$-aryl)-($C_2$-$C_6$-alkenyl-), wherein the ($C_6$-$C_{14}$-aryl)-($C_2$-$C_6$-alkenyl-) is optionally substituted on the $C_2$-$C_6$-alkenyl or the $C_6$-$C_{14}$-aryl.

As used herein, the term "neurotransmitter" includes, but is not limited to norepinephrine, glutamate, dopamine, gamma-aminobutyric acid, serotonin, and an endorphin. In a specific, non-limiting example, the moiety G that is photoreleased is glutamate, as shown in Scheme IV:

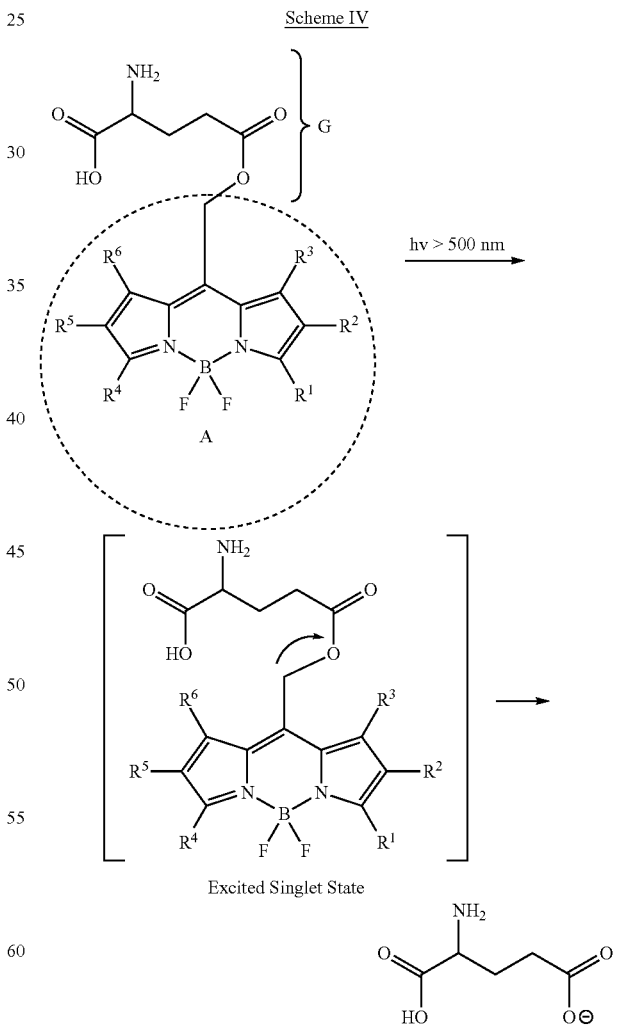

wherein the moiety A is depicted within the broken circle; and $R^1$, $R^2$, $R^3$, $R^4$, $R^5$, and $R^6$ are each, independently, hydrogen, halogen, optionally substituted $C_1$-$C_6$-alkyl, optionally substituted $C_2$-$C_6$-alkenyl or ($C_6$-$C_{14}$-aryl)-($C_2$-$C_6$-alkenyl-), wherein the ($C_6$-$C_{14}$-aryl)-($C_2$-$C_6$-alkenyl-) is optionally substituted on the $C_2$-$C_6$-alkenyl or the $C_6$-$C_{14}$-aryl.

In some embodiments, G is not acetate ($CH_3COO^-$).

Embodiments of the present invention also relate to compounds of the formula A-G, wherein the moiety A is a moiety of the formula I:

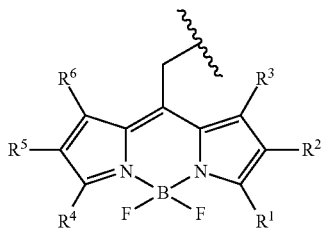

I wherein:
the wavy line represents the attachment point of the moiety A to the moiety G; $R^1$, $R^2$, $R^3$, $R^4$, $R^5$, and $R^6$ are each, independently, hydrogen, halogen, optionally substituted $C_1$-$C_6$-alkyl, optionally substituted $C_2$-$C_6$-alkenyl or $C_2$-$C_6$-alkenyl-$C_6$-$C_{14}$-aryl, wherein the $C_2$-$C_6$-alkenyl-$C_6$-$C_{14}$-aryl is optionally substituted on the $C_2$-$C_6$-alkenyl or the $C_6$-$C_{14}$-aryl; and wherein at least one of $R^1$, $R^2$, $R^3$, $R^4$, $R^5$, and $R^6$ is bromine or iodine.

In some embodiments, $R^2$ and $R^5$ are each, independently, bromine or iodine. In some embodiments, $R^2$ and $R^5$ are each bromine. In other embodiments, $R^2$ and $R^5$ are each iodine. In still other embodiments, $R^2$ and $R^5$ are each, independently, bromine or iodine and $R^1$, $R^3$, $R^4$, and $R^6$ are each, independently, an optionally substituted $C_1$-$C_6$-alkyl. In still other embodiments, $R^2$ and $R^5$ are each, independently, bromine or iodine and $R^1$, $R^3$, $R^4$, and $R^6$ are each methyl.

The Linkage Between Moiety "A" and "G"

As stated herein, the moieties A and G in compounds of the formula A-G can be photoreleasably linked directly or indirectly by any suitable means (e.g., covalently via ether, amine, ester, amide or carbamate linkages, or the like). Direct linkages between the moieties A and G are specifically exemplified in Schemes I-IV. In those specific cases, the moiety G is linked through a —$CH_2$—NH— linkage (Scheme I); through a —$CH_2$—O— linkage (Schemes II and III); and through a —$CH_2$—O—C(O)— linkage (Scheme IV); where the —NH— group; the —O— group; and the —O—C(O)— groups are part of the moiety G.

The moieties A and G in compounds of the formula A-G can also be photoreleasably linked indirectly via a linking group L in a compound of the formula A-$L_x$-G (wherein x is 0 or 1) where the linking group can be any suitable linking group including, but not limited to, acylalkylacyloxy (e.g., —O—C(O)($CH_2$)$_n$C(O)—, wherein n is an integer from 0 to 6); acylalkyloxy (e.g., —O—($CH_2$)$_n$C(O)—, wherein n is an integer from 0 to 6); (poly)alkylene glycol (e.g., [—O—($CH_2$)$_m$—O—]$_p$, wherein m is an integer from 1 to 3 and p is an integer from 1 to 20); aminoalkylamino (e.g., —$NR^7$—($CH_2$)$_n$—$NR^7$—, wherein n is an integer from 0 to 6 and each $R^7$ is independently H or $C_1$-$C_6$-alkyl); aminoalkyloxy (e.g., —O—($CH_2$)$_n$—$NR^7$—, wherein n is an integer from 0 to 6 and $R^7$ is H or $C_1$-$C_6$-alkyl); acylalkylamino (e.g., —$NR^7$—($CH_2$)$_n$C(O)—, wherein n is an integer from 0 to 6 and $R^7$ is H or $C_1$-$C_6$-alkyl); and the like, wherein the "alkyl" in acylalkylacyloxy, acylalkyloxy, (poly)alkylene glycol, aminoalkylamino, aminoalkyloxy, and acylalkylamino is optionally substituted. Those of skill in the art will recognize that when x in a compound of the formula A-$L_x$-G is 1, the group that is photoreleased is L-G. Those of skill in the art will also recognize that the linking groups exemplified herein can link the moieties A and G in the direction shown or in the opposite direction. For example, when L is —O—($CH_2$)$_n$—$NR^7$—, the compound of the formula A-L-G can be A-O—($CH_2$)$_n$—$NR^7$-G or A-$NR^7$—($CH_2$)$_n$—O-G.

In some embodiments, the compounds of the formula A-G are thermally stable. As used herein, the term "thermally stable" refers to compounds where there is no substantial change in the $^1H$ NMR spectrum of a compound of the formula A-G after boiling the compound in methanol for 1 hour in a foil-wrapped vessel.

The compounds and methods of the various embodiments of the present invention can be used to study, among other things, biological systems and how those systems react when the moiety G is, or a fragment thereof, is photoreleased from a compound of the formula A-G. For example, the compounds of the formula A-G can be used to probe neuronal circuits, neuronal integration, and synaptic plasticity when the moiety G comprises a neurotransmitter such as glutamate and gamma aminobutyric acid (GABA). See Dynamic Studies in Biology 212-247 (Maurice Goeldner and Richard Givens eds., Wiley VCH Verlag GmbH & Co. KGaA 2005), which is incorporated by reference as if fully set forth herein.

EXAMPLES

The present invention can be better understood by reference to the following examples which are offered by way of illustration. The present invention is not limited to the examples given herein.

Examples of compounds of the formula A-G of the various embodiments of the present invention include the compounds numbered 1-4, which are commercially available from Exciton (Dayton, Ohio):

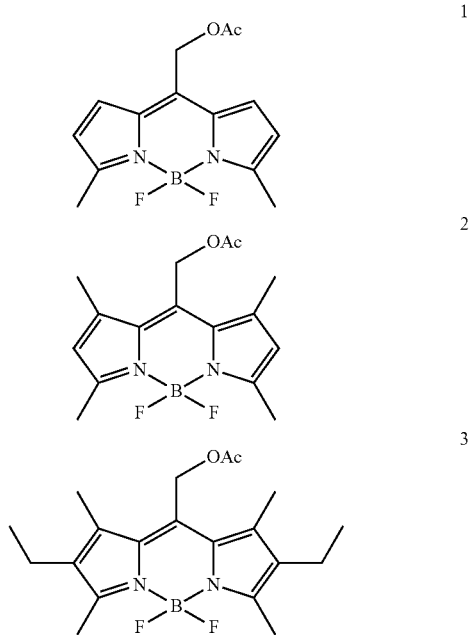

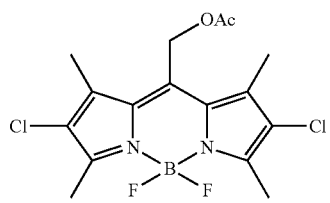

4

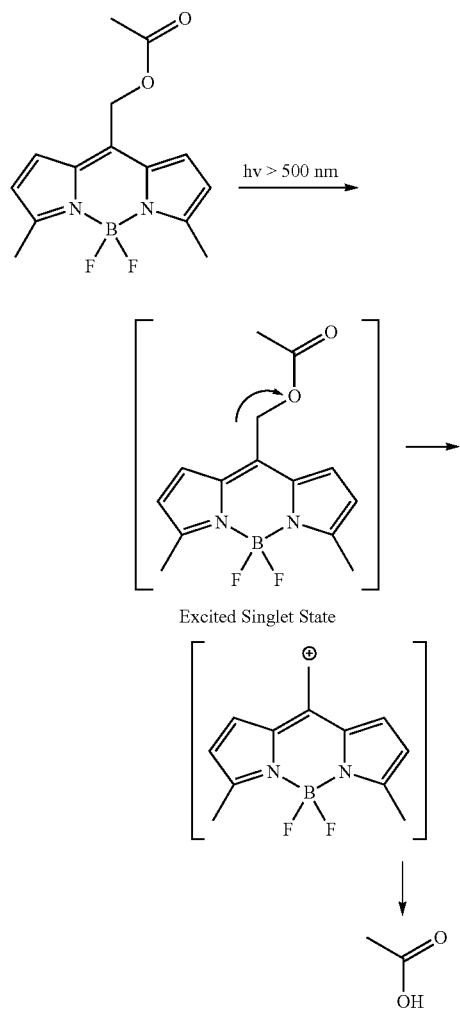

While not wishing to be bound by any specific theory, it is believed that irradiating a composition comprising the compounds of the formula A-G described herein (including the compounds 1-7) at a wavelength of >500 nm excites such compounds to their excited singlet state. It is believed that these compounds have excited singlet states with considerable diradical character. The excited singlet state undergoes heterolysis to generate an anion and a carbocation (see Scheme V herein, with compound 1 as an example; compounds 2-7 will undergo a similar transformation that releases acetic acid) that may be described as having ion diradical character rather than a closed-shell carbocation.

Example 1: Synthesis of Compound 5 from Compound 2

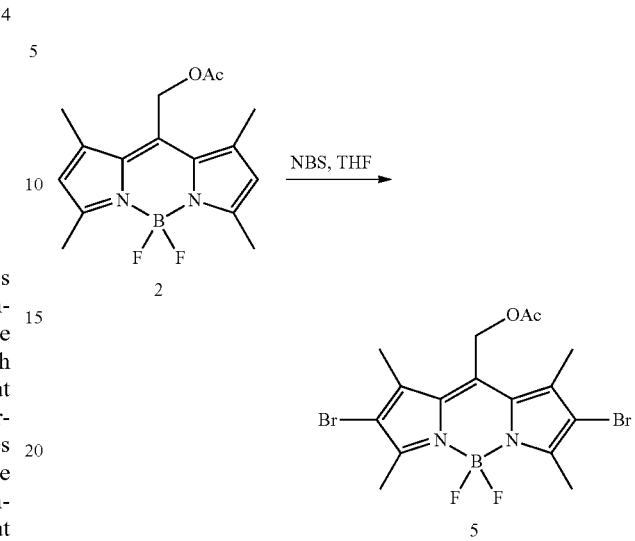

Synthesis of compound 5: Compound 2 (0.1 g, 0.31 mmol, 1 eq.), was dissolved in 3 mL of dry THF under argon and cooled to −78° C. N-bromosuccinimide (0.23 g, 1.25 mmol, 4 eq.) dissolved in 2 mL of dry THF was added dropwise to the solution. The reaction mixture was stirred for 15 min. at −78° C., after which it was warmed to room temperature and stirred for an additional 5 h. The solvent was evaporated under reduced pressure. The solid residue was loaded onto a silica gel flash column and eluted with hexane-ethyl acetate 90:10 v/v to give compound 5 as dark red crystals (0.14 g, 95% yield); mp 230° C. (decomp); $^1$H NMR (600 MHz, CDCl$_3$): δ 5.32 (s, 2H), 2.63 (s, 6H), 2.40 (s, 6H), 2.15 (s, 3H); $^{13}$C NMR (150 MHz, CDCl$_3$) δ 170.45, 155.29, 138.93, 133.85, 131.87, 113.10, 58.04, 20.69, 14.94, 14.08; HRMS (ESI) for formula C$_{16}$H$_{17}$BBr$_2$F$_2$N$_2$O$_2$Na$^+$, Calc. 497.9646, Found 497.9646.

Example 2: Synthesis of Compound 6 from Compound 2

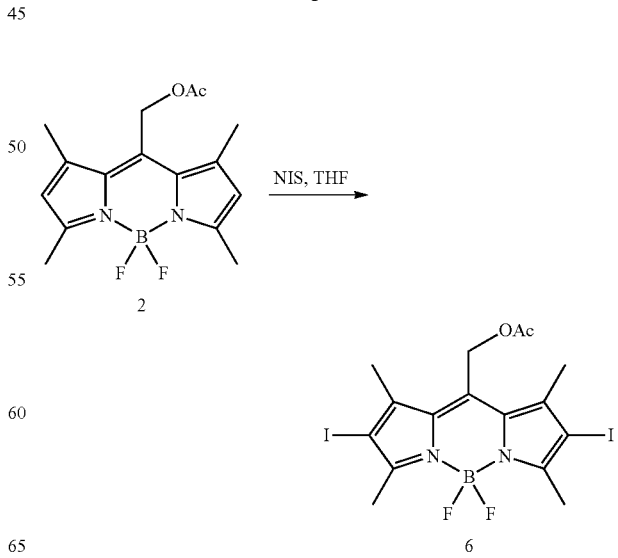

Synthesis of compound 6: Compound 2 (0.1 g, 0.31 mmol, 1 eq.), was dissolved in 3 mL dry THF under argon and cooled to −78° C. N-iodosuccinimide (0.18 g, 2.5 mmol, 4 eq.) dissolved in 2 mL of dry THF was added dropwise to the solution. The reaction mixture was stirred for 15 min at −78° C., after which it was warmed to room temperature and stirred for an additional 5 h. The solvent was evaporated under reduced pressure. The solid residue was loaded onto a silica gel flash column and eluted with dichloromethane to give 6 as dark purple crystals (0.07 g, 39% yield); mp 210° C.; $^1$H NMR (600 MHz, CDCl$_3$): δ 5.31 (s, 2H), 2.59 (s, 6H), 2.38 (s, 6H), 2.14 (s, 3H); $^{13}$C NMR (150 MHz, CDCl$_3$) δ 170.43, 158.06, 143.60, 132.92, 132.70, 87.38, 58.35, 20.68, 18.29, 16.47; MS (ESI) for formula C$_{16}$H$_{17}$BI$_2$F$_2$N$_2$O$_2$Na$^+$, Calc. 593.9369, Found 593.9378.

Example 3: Synthesis of Compound 7

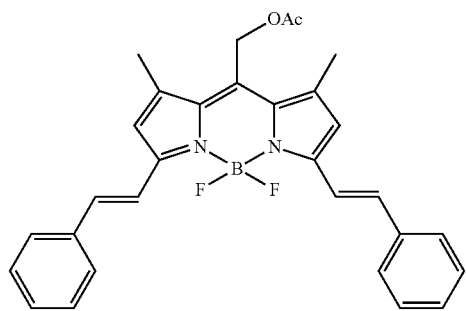

Prepared an ethanol solution (8 mL) of 40 mg (0.125 mmol) of Compound 2, 60 μL (0.661 mmol) of benzaldehyde, 150 μL of piperidine and 150-μL of acetic acid. The solution was placed in a microwave reaction vessel. The vessel was sparged with argon and then heated in a microwave at 113° C. for 10 minutes at 800 watt power. The reaction mixture was concentrated under reduced pressure and purified by silica column chromatography (80:20 hexanes:ethyl acetate), giving 32 mg of Compound 7 as a purple solid (58%).

Example 4

The observed substrate release rate as a function of photolysis time is quantified by the quantum efficiency parameter (εΦ), which is the product of the extinction coefficient at the irradiation wavelength (ε) and the quantum yield (Φ). Extinction coefficients for compounds 1-6 were determined by UV-Vis spectroscopy (see Table 1).

TABLE 1

Optical properties and quantum efficiencies of compounds 1-6

| Compound | $\lambda_{max}$ (nm) | $\lambda_{em}$ (nm) | ε (×10$^4$ M$^{-1}$ cm$^{-1}$) | Φ (×10$^{-4}$) | εΦ (M$^{-1}$cm$^{-1}$) |
|---|---|---|---|---|---|
| 1 | 519 | 527 | 5.7 | 6.4 | 37 |
| 2 | 515 | 526 | 7.1 | 9.9 | 70 |
| 3 | 544 | 560 | 6.2 | 9.5 | 59 |
| 4 | 544 | 570 | 4.8 | 4.0 | 19 |
| 5 | 545 | 575 | — | — | — |
| 6 | 553 | 576 | 4.9 | 23.8 | 117 |

To compute the quantum yields of photorelease (Φ), the flux of a 532 nm laser excitation beam (ND:YAG, 1st harmonic) was determined using potassium ferrioxalate actinometry. Release of acetic acid as a function of laser irradiation time in methanol was followed by quantitative LC/UV methods known in the art. Each quantum yield reported is the average of 3 separate runs. Identical actinometry measurements performed after photolysis demonstrated high flux stability of the laser. Additionally, repeating the quantum yield measurement for compound 2 on a different day with a different laser power setting (in triplicate) gave an identical value for the quantum yield, indicating reproducibility.

Unlike compounds 1-4 and 6, the brominated compound 5 was found to be unstable. It decomposes after 1 day stored on the shelf in the dark, and photolysis of freshly prepared and purified compound 5 led to secondary products in addition to acetic acid release. In addition, photolysis was accompanied by rapid solution bleaching. Quantum yield measurements for compound 5 were therefore excluded from Table 1.

In general, the quantum efficiencies for compounds 1-4 and 6 are comparable with caged o-nitrobenzyl systems. See, e.g., Petr Klán et al., Chem. Rev. 113: 119-191 (2013), which is incorporated by reference as if fully set forth herein. Even thought the quantum yields for compounds 1-4 are lower than those for some o-nitrobenzyl photocaged structures, this lower quantum yield is compensated by the much higher extinction coefficients of the BODIPY chromophores compared to the o-nitrobenzyl chromophore, leading to reasonable quantum efficiencies. The iodinated derivative compound 6 has the largest quantum efficiency, comparable to that of some caged o-nitrobenzyl systems, but with a $\lambda_{max}$ at ~550 nm rather than in the UV (the parent o-nitrobenzyl system has a $\lambda_{max}$ of ~280 nm while some dimethoxy analogs have a $\lambda_{max}$ of ~350 nm). While not being bound by any particular theory, it is plausible that the higher quantum yield of compound 6 occurs because the iodine atoms promote intersystem crossing to a triplet state, which are usually longer lived than excited states. Given that the triplet state of the corresponding carbocation is the computed ground state by ~5 kcal/mol, it is certainly energetically reasonable that heterolysis could occur in the triplet excited state leading to the triplet "carbocation," similar to the phenacyl photocage derivatives described by Givens et al., Can. J. Chem. 89: 364-384 (2011), which is incorporated by reference as if fully set forth herein. This hypothesis is supported by the very weak fluorescence of solutions of compounds 5 and 6, compared to solutions of compounds 1-4.

Example 5

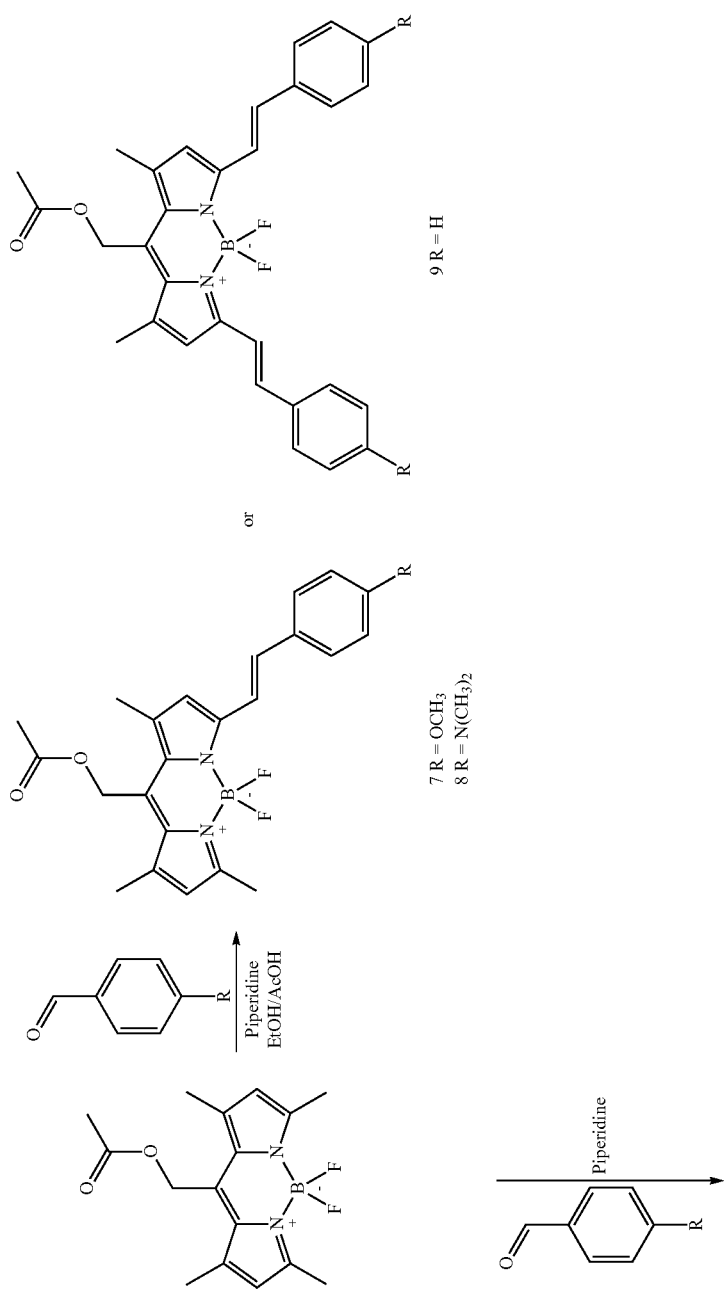

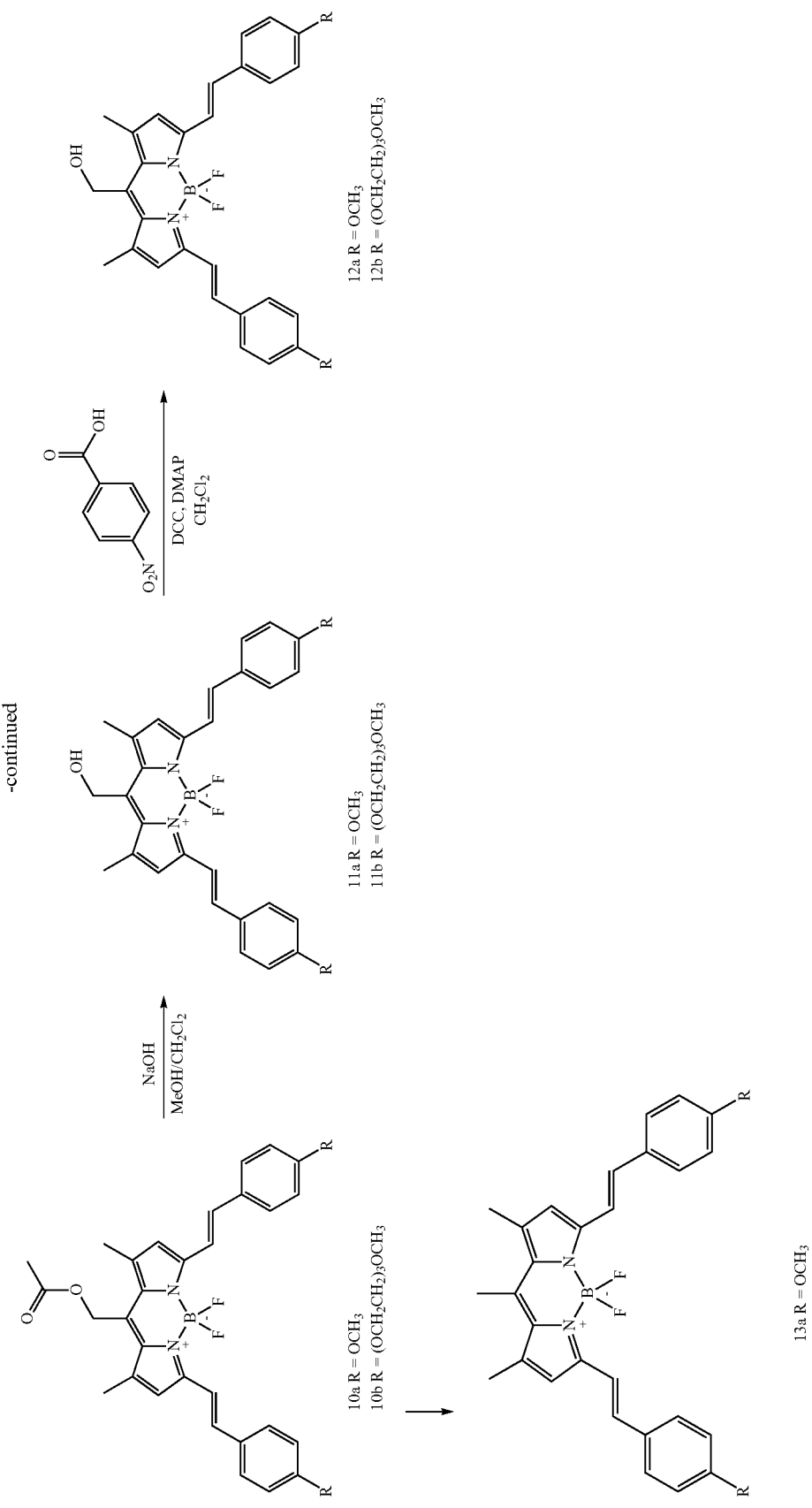

General Procedure For Compounds 7-9

8-Acetoxymethyl-1,3,5,7-tetramethyl pyrromethene fluoroborate (50 mg, 0.016 mmol, 1 eq.) and the respective benzaldehyde (0.032 mmol, 2 eq.) were added to 8 mL of ethanol which had been previously dried over 3 Å molecular sieves for 24 h. This suspension was then placed in a dry, glass microwave reaction vessel. Acetic acid (120 μL) and piperidine (120 μL) were then added and the vessel was sparged with argon. The microwave vessel was irradiated at 113° C. and 800 W for the times listed below. The solvent was evaporated under reduced pressure and purified as detailed herein.

8-Acetoxymethyl-3-(4-methoxy)styryl-1,5,7-trimethyl pyrromethene fluoroborate 7

8-Acetoxymethyl-1,3,5,7-tetramethyl pyrromethene fluoroborate (50 mg, 0.016 mmol, 1 eq.) and 4-methoxybenzaldehyde (4.4 mg, 0.032 mmol, 2 eq.) were irradiated for 10 min. The solid residue was loaded onto a silica gel flash column and eluted with 50:50 hexanes:ethyl acetate. The dark purple product (32 mg, 0.009 mmol) was recovered and further purified using a prep TLC plate and 80:20 hexanes: ethyl acetate in 58% yield. $^1$H NMR (400 MHz, CDCl$_3$): δ=7.55 (d, J=4 Hz, 2H), 7.52 (d, J=8 Hz, 1H), 7.24 (d, J=8 Hz, 1H), 6.91 (d, J=4 Hz, 2H), 6.71 (s, 1H), 6.11 (s, 1H), 5.3:3 (s, 2H), 3.85 (s, 3H), 2.58 (s, 3H), 2.43 (s, 3H), 2.28 (s, 3H), 2.15 (s, 3H) ppm; $^{13}$C NMR (200 MHz, CDCl$_3$): δ=170.7, 160.8, 155.5, 154.5, 1.41.1, 140.4, 137.3, 135.4, 134.5, 132.9, 131.4, 129.4, 122.2, 118.9, 117.0, 114.5, 58.2, 55.2, 20.8, 16.1, 15.7, 14.9 ppm; Hi-res MS (ESI) for formula C$_{24}$H$_{25}$BF$_2$N$_2$O$_3$, Calc. 438.2035, Found 438.2038.

8-Acetoxymethyl-3-(4-dimethylamino)styryl-1,5,7-trimethyl pyrromethene fluoroborate 8

8-Acetoxymethyl-1,3,5,7-tetramethyl pyrromethene fluoroborate (50 mg, 0.016 mmol, 1 eq.) and 4-(dimethylamino) benzaldehyde (4.8 mg, 0.032 mmol, 2 eq.) were irradiated for 20 min. The solid residue was loaded onto a silica gel flash column and eluted with 80:20 hexanes:ethyl acetate to give 8 as a dark blue solid (9.1 mg, 24% yield). $^1$H NMR (400 MHz, CDCl$_3$): δ=7.50 (d, J=8 Hz, 2H), 7.45 (d, J=16 Hz, 1H), 7.24 (d, J=16 Hz, 1H), 6.72 (s, 1H), 6.68 (d, J=8 Hz, 2H), 6.07 (s, 1H), 5.32 (s, 2H), 3.04 (s, 6H), 2.57 (s, 3H), 2.41 (s, 3H), 2.36 (s, 3H), 2.15 (s, 3H) ppm; $^{13}$C NMR (200 MHz, CDCl$_3$): δ=170.9, 156.1, 153.4, 151.4, 141.4, 139.2, 138.6, 134.9, 132.3, 129.7, 124.6, 121.4, 119.2, 114.3, 112.1, 58.3, 40.4, 24.0, 20.9, 16.1, 15.6 ppm; Hi-res MS (ESI) for formula C$_{25}$H$_{28}$BF$_2$N$_3$O$_2$, Calc. 451.2352, Found 451.2339.

8-Acetoxymethyl-3,5-bisstyryl-1,7-dimethyl pyrromethene fluoroborate 9

8-Acetoxymethyl-1,3,5,7-tetramethyl pyrromethene fluoroborate (50 mg, 0.016 mmol, 1 eq.) and benzaldehyde (3.4 mg, 0.032 mmol, 2 eq.) were irradiated in the microwave for 20 min. The solid residue was loaded onto a silica gel flash column and eluted with 80:20 hexanes:ethyl acetate to give 9 as a dark blue solid (23.7 mg, 38% yield). $^1$H NMR (400 MHz, CDCl$_3$): δ=7.71 (d, J=8 Hz, 2H), 7.64, (d, J=4 Hz, 4H), 7.42 (t, J=8 Hz, 4H), 7.34 (t, J=8 Hz, 2H), 7.30 (d, J=8 Hz, 2H), 6.77 (s, 2H), 5.37 (s, 2H), 2.44 (s, 6H), 2.17 (s, 3H) ppm; $^{13}$C NMR (200 MHz, CDCl$_3$): δ=170.6, 153.4, 140.4, 136.4, 134.8, 130.2, 129.2, 128.8, 127.7, 118.9, 58.0, 22.7, 15.9, 14.1 ppm; Hi-res MS (ESI) for formula C$_{30}$H$_{27}$BF$_2$N$_2$O$_2$Na$^+$, Calc. 519.2026, Found 519.2041.

8-Acetoxymethyl-3,5-bis(4-methoxy)styryl-1,7-dimethyl pyrromethene fluoroborate 10a 8-Acetoxymethyl-1,3,5,7-tetramethyl pyrromethene fluoroborate (25 mg, 0.078 mmol, 1 eq.), p-anisaldehyde (0.5 mL, 4.1 mmol, 50 eq.), and one drop piperidine were added to a 20 mL scintillation vial. The vial was stirred under vacuum at 60° C. until the color changed from red to blue-green (TIME NEEDED). The mixture was returned to room temperature and loaded onto silica gel flash column and eluted with 80:20 hexanes:ethyl acetate followed by 50:50 hexanes:ethyl acetate to give 10a (30 mg, 69% yield). $^1$H NMR (400 MHz, CDCl$_3$): δ=7.59 (d, J=4 Hz, 4H), 7.58 (d, J=8 Hz, 2H), 7.24 (d, J=8 Hz, 2H), 6.94 (d, J=4 Hz, 4H), 6.73 (s, 2H), 5.35 (s, 2H), 3.87 (s, 6H), 2.43 (s, 6H), 2.16 (s, 3H) ppm; $^{13}$C NMR (200 MHz, CDCl$_3$): δ=170.8, 160.7, 153.5, 140.1, 136.7, 134.7, 129.6, 129.4, 118.8, 117.2, 114.5, 58.3, 55.5, 20.9, 16.0 ppm; Hi-res MS (ESI) for formula C$_{32}$H$_{31}$BF$_2$N$_2$O$_4$, Calc. 556.2454, Found 556.2451.

8-Acetoxymethyl-3,5-bis(4-(1,4,7,10-tetraoxaundecyl)styryl-1,7-dimethyl pyrromethene fluoroborate 10b 8-Acetoxymethyl-1,3,5,7-tetramethyl pyrromethene fluoroborate (22 mg, 0.068 mmol, 1 eq.) and 4-(1,4,7,10-Tetraocaundecyl)benzaldehyde (182 mg, 0.68 mmol, 10 eq.) were added to a 20 mL scintillation vial with 1 drop piperidine and stirred at 60° C. under vacuum until the reaction was complete by TLC. The oil was purified by silica gel flash chromatography with 100:1 dichloromethane:methanol to give 27 mg pure 10b (49% yield). $^1$H NMR (500 MHz, CDCl$_3$): δ=7.56 (m, 6H), 7.23 (d, J=16 Hz, 2H), 6.94 (d, J=8 Hz, 4H), 6.71 (s, 2H), 5.33 (d, 2H), 4.18 (t, J=5, 4H), 3.88 (t, J=5, 4H), 3.75 (m, 4H), 3.71 (m, 4H), 3.70 (m, 4H), 3.67 (m, 4H), 3.56 (m, 4H), 3.38 (s, 6H), 2.41 (s, 6H), 2.14 (s, 3H) ppm; $^{13}$C NMR (500 MHz, CDCl$_3$): δ=170.8, 159.9, 153.5, 140.0, 136.7, 134.7, 129.7, 129.3, 129.2, 118.8, 117.2, 115.1, 72.1, 71.0, 70.8, 70.7, 69.8, 67.9, 67.8, 67.7, 59.2, 58.3, 29.8, 20.9, 16.0 ppm; Hi-res MS (ESI) for formula C$_{44}$H$_{55}$BF$_2$N$_2$O$_{10}$Na$^+$, Calc. 842.3846, Found 842.3845.

General Procedure for Compounds Compound 11a-b

Compound 4a-b in the amounts listed below were dissolved in 1:1 dichloromethane:methanol to which was added 0.1 M aqueous sodium hydroxide to make 0.01 M solution. The reaction mixtures was stirred at room temperature for the times listed below after which they were diluted with 20 mL dichlochloromethane, washed with brine 3x, dried over sodium sulfate, filtered, and the solvent was evaporated under vacuum. The remaining solids were purified as listed below.

3,5-Bis(4-methoxy)styryl-1,7-dimethyl-8-hydroxymethyl pyrromethene fluoroborate 11a Compound 10a (55 mg, 0.10 mmol, 1 eq.) was dissolved in 20 mL 1:1 dichloromethane:methanol to which was added 3 mL 0.1 M aqueous sodium hydroxide. The reaction was stirred for 2 hours and the dark blue solid was purified by flash chromatography with dichloromethane as the eluent to give 35 mg of 11a (70% yield). $^1$H NMR (400 MHz, CDCl$_3$): δ=7.59 (m, 6H), 7.26 (d, J=16 Hz, 2H), 6.94 (d, J=8 Hz, 4H), 6.73 (s, 2H), 4.95 (s, 2H), 3.86 (s, 6H), 2.57 (s, 6H).

$^{13}$CNMR (200 MHz, CDCl$_3$): δ=160.74, 153.43, 140.13, 136.43, 134.41, 134.22, 139.72, 139.30, 118.60, 117.43, 117.41, 117.39, 114.51, 90.17, 56.18, 55.55, 29.86, 15.96, 1.17 ppm; Hi-res MS (ESI) for formula C$_{30}$H$_{29}$BF$_2$N$_2$O$_3$ H+, Calc. 515.2310, Found. 515.2302.

3,5-Bis(4-(1,4,7,10-tetraoxaundecyl)styryl-1,7-dimethyl-8-hydroxymethyl pyrromethene fluoroborate 11b Compound 10b (35 mg, 0.04 mmol, 1 eq.) was dissolved in 40 mL 1:1 dichloromethane:methanol to which was added 5 mL 0.1 M aqueous sodium hydroxide. The remaining solid was purified on silica gel flash chromatography using a gradient from 0.5-2% methanol in dichloromethane as the eluent to give 19 mg of pure 11b (57% yield). $^1$HNMR (500 MHz, CDCl$_3$): δ=7.53 (m, 6H), 7.17 (d, J=17 Hz, 2H), 6.91 (d, J=9 Hz, 4H), 4.85 (s, 2H), 4.15 (t, J=5 Hz, 4H) 3.87 (t, J=5 Hz, 4H), 3.74 (m, 4H), 3.69 (m, 4H), 3.65 (m, 4H) 3.55 (m, 4H), 3.37 (s, 6H), 2.50 (s, 6H) ppm; $^{13}$CNMR (125 MHz, CDCl$_3$): δ=159.8, 153.1, 140.2, 136.3, 134.4, 134.2, 132.1, 129.7, 129.2, 118.5, 117.2, 115.0, 72.1, 71.0, 70.8, 70.7, 69.8, 67.6, 59.2, 55.9, 29.8, 15.88 ppm; Hi-res MS (ESI) for formula C$_{42}$H$_{53}$BF$_2$N$_2$O$_9$, Calc. 779.3885, Found 779.3878.

3,5-bis(4-methoxy)styryl-1,7-dimethyl-8-(2,4-nitrobenzoato)pyrromethene fluoroborate 12a A 100 mL 2-neck round bottom flask was charged with 2,4-dinitrobenzoic acid (25 mg) dissolved in 2 mL dry DCM and stirred under argon. DCC (20 mg) dissolved in 2 mL DCM was added dropwise. DMAP (1 mg) was then added followed by 11a (50 mg) dissolved in 2 mL dry DCM. The solution was stirred for 3.5 h after which the solvent was removed under vacuum and the remaining solid was purified by column chromatography with dichloromethane as the eluent to give pure 12a (35 mg, 53% yield). $^1$HNMR (400 MHz, CDCl$_3$): δ=8.87 (s, 1H), 8.55 (d, J=8 Hz, 1H), 7.88 (d, J=8 Hz, 1H), 7.58 (d, J=8 Hz, 6H), 7.54 (d, J=12 Hz, 2H), 6.96 (m, 6H), 6.75 (s, 2H), 5.75 (s, 2H), 3.86 (s, 6H), 2.51 (s, 6H) ppm; $^{13}$CNMR (200 MHz, DMSO): δ=163.24, 160.46, 152.79, 149.04, 147.19, 140.43, 137.56, 133.81, 131.51, 130.39, 128.96, 128.65, 128.53, 127.82, 119.91, 119.34, 115.69, 114.67, 59.95, 55.40, 15.34 ppm; Hi-res MS (ESI) for formula C$_{37}$H$_{31}$BF$_2$N$_4$O$_8$, Calc. 708.2203, Found 708.2217.

3,5-Bis(4-(1,4,7,10-tetraoxaundecyl)styryl-1,7-dimethyl-8-(4-nitrobenzoato)pyrromethene fluoroborate 12b N,N'-dicyclohexylcarbodiimide (10 mg, 0.04 mmol, 1.6 eq.) dissolved in 2 mL dichloromethane was added slowly to a solution of 4-nitrobenzoic acid (7 mg, 0.04 mmol, 1.6 eq.) and 4-dimethylaminopyridine (1 mg, 0.008 mmol, 0.4 eq.) stirring in dry dichloromethane under argon. Next, 11b (19 mg, 0.025 mmol, 1 eq.), dissolved in 2 mL dichloromethane, was added dropwise to the solution and it was stirred for 30 min. The solvent was removed under vacuum and the remaining mixture was purified by prep HPLC to give pure 7 (20 mg, 84% yield). $^1$HNMR (400 MHz, CDCl$_3$): δ=8.30 (d, J=9 Hz, 2H), 8.25 (d, J=9 Hz, 2H), 7.58 (m, 6H), 7.25 (d, J=16 Hz, 2H), 6.95 (d, J=7 Hz, 4H), 6.74 (s, 2H), 5.64 (s, 2H), 4.19 (t, J=5 Hz, 4H), 3.89 (t, J=5 Hz, 4H), 3.76 (m, 4H), 3.69 (m, 8H), 3.57 (m, 4H), 3.39 (s, 6H), 2.43 (s, 6H) ppm; $^{13}$CNMR (125 MHz, CDCl$_3$): δ=164.6, 160.1, 153.8, 151.0, 139.9, 137.1, 134.8, 134.5, 131.2, 129.6, 129.4, 127.9, 123.9, 119.0, 117.1, 115.1, 90.1, 72.1, 71.0, 70.8, 70.7, 69.8, 67.7, 59.6, 59.2, 16.1 ppm; Hi-res MS (ESI) for formula C$_{49}$H$_{56}$BF$_2$N—$_3$O$_{12}$Na$^+$, Calc. 949.3854, Found 949.3831.

3,5-Bis(4-methoxy)styryl-1,7,8-trimethyl pyrromethene fluoroborate 13

Compound 10a (30 mg, 0.054 mmol, 1 eq.), dissolved in 2 mL dry methylene chloride, was added to a suspension of nickel (II) chloride (16 mg, 0.12 mmol, 2.2 eq.) in 10 mL freshly distilled methanol. Sodium borohydride (10 mg, 0.24 mmol, 4.4 eq.) was added portionwise. The reaction was stirred for 2 hours at room temperature after which 10 mL saturated ammonium chloride was added. The solution was extracted 3 times with methylene chloride. The combined organic layers were dried over sodium sulfate, filtered, and the solvent was removed under vacuum. The remaining mixture was purified by flash chromatography with 70:30 methylene chloride:toluene to give pure 13 (8.4 mg, 28% yield). $^1$HNMR (400 MHz, CDCl$_3$) δ=7.58 (m, 6H), 7.20 (d, J=16 Hz, 2H), 6.92 (d, J=8 Hz, 4H), 669 (s, 2H), 3.85 (s, 6H), 2.63 (s, 3H), 2.48 (s, 6H) ppm; Hi-res MS (ESI) for formula C$_{30}$H$_{28}$BF$_2$N$_2$O$_2$, Calc. 497.2321, Found 497.2317.

Example 6: Quantum Yield Studies

All quantum yields were carried out using a liquid-phase potassium ferrioxalate actinometer. The actinometer was prepared by mixing three volumes of 1.5 M K$_2$C$_2$O$_4$ solution with one volume of 1.5 M FeCl$_3$ solution in water, and stirring in complete darkness. The precipitated K$_3$Fe(C$_2$O$_4$)$_3$.3H$_2$O was then recrystallized three times from hot water and dried in a current of warm air. To prepare 1 L of 0.15M K$_3$Fe(C$_2$O$_4$)$_3$.3H$_2$O solution, 73.68 g of the precipitate was dissolved in 800 mL water; 100 mL 1.0 N sulfuric acid was added and filled to the mark with water, again in complete darkness. For all quantitative work the preparation and manipulation of the ferrioxalate solutions must be carried out in a darkroom, using a red light. The light intensity in a photochemical reaction is determined by irradiating ferrioxalate solution and monitoring the subsequent change in absorbance at 510 nm. Irradiation was conducted using 532 nm excitation from a ND:YAG laser source (1$^{st}$ harmonic). Autopipettes were used to ensure all volumes were accurately measured.

For each actinometric measurement a methacrylate cuvette was filled with 3 mL of 0.15 M ferrioxalate solution. The cell was placed in the sample holder, stirred and irradiated for a set period of time (0, 0.25, 0.50, 0.75, 1, 2, 3 minutes). After the allocated irradiation time the solution was transferred into a 25 mL volumetric flask, to which was added in sequence 6 mL of a developer solution (0.05 mol % phenanthroline/0.75 M acetate/0.2 M sulfuric acid), 5 mL 1 M sodium fluoride solution in water. The sample was diluted to 25 mL with water, mixed and allowed to incubate for 10 minutes. After the incubation period was complete, 3 mL of sample was transferred into 1 cm methacrylate cuvette and the absorbance (at 510 nm) read using a spectrophotometer.

Using iron sulfate standard solutions between 1.6×10$^{-5}$ M to 9.6×10$^{-5}$ M, a standard curve based on absorbance of the ferrioxalate/phenanthroline complex at 510 nm was compiled and the irradiated samples absorbances were compared to yield the concentration iron (II) cleaved via photolysis within the timescale of experiment.

The flux of the laser was calculated the following equations:

$$I = \frac{\Delta n}{(10^{-3} \cdot \Phi \cdot V_1 \cdot t)}$$

where I is the flux (Einstein/L/s), $\Delta n$ is the $Fe^{2+}$ photogenerated (mole), $\varphi$ is the quantum yield at 532 nm, $V_1$ is the irradiated volume (mL), and t=irradiation time (seconds);

$$\Delta n = \frac{10^{-3} \cdot V_1 \cdot V_3 \cdot C_T}{V_2}$$

where $V_2$ is the volume taken from the irradiated sample (mL), $V_3$ is the volume after dilution for concentration determination (mL), and $C_T$ is the concentration of $Fe^{2+}$ after dilution (M); and $$C_T = \frac{abs}{\varepsilon \cdot l}$$

where abs is the absorbance at 510 nm, $\varepsilon$ is the molar absorptivity ($M^{-1}$ $cm^{-1}$) and l is the path length.

Due to the low absorbance of the potassium ferrioxalate solution at 532 nm, a correction was made to account for an absorbance less than 2 (multiplied the flux by 0.0967).

For Compounds 1-4a

For each compound, a solution of 1000 ppm was prepared using 1 mg of sample and dissolving in 1 mL methanol. Due to solubility issues samples were predissolved in 20 µL of acetonitrile and injected into the 1 mL of methanol. Each sample cuvette was placed in the sample holder and irradiated for a specified period of time (so as not to exceed 30% cleavage). At each time point selected, 10 µL of the irradiated solution was removed and placed into a LC vial fitted with a 250 µL glass vial insert fitted with polymer feet.

LC-UV was conducted for all samples using an XDB-C18 column and monitoring the absorbance at 210 nm with 2 µL of sample injected. The eluent system was a 1 mmol/L sulfuric acid:8 mmol/L sodium sulfate (made using 54.3 µL concentrated sulfuric acid and 1.1370 g sodium sulfate in 1 L of water). For Compounds 7-10a, a flow rate of 0.8 mL/min was used where the acidic buffer was ran for 25 minutes.

Using acetic acid standard solutions between 5-1000 ppm, a standard curve based on the LC-UV integration of acetic acid was compiled and the irradiated samples peak integrations were compared to yield the concentration of acetic acid cleaved via photolysis within the timescale of experiment.

Optical properties and quantum efficiencies of compounds 7-9, 10a-b, 11b, 2, and 6 are given in Table 2. Quantum yields of acetic acid release ($\Phi$) determined by ferrioxalate actinometry in MeOH with a 532 nm ND:YAG laser source and release followed using quantitative LC-UV ($\Phi$ values are the average of 3 runs).

TABLE 2

Optical properties and quantum efficiencies of compounds 7-9, 10a-b, 11b, 2, and 6

| | $\lambda_{max}$ (nm) | $\lambda_{em}$ (nm) | $\varepsilon$ ($\times 10^4$ $M^{-1}$ $cm^{-1}$) | $\Phi$ ($\times 10^{-4}$) | $\varepsilon\Phi$ ($M^{-1}cm^{-1}$) |
|---|---|---|---|---|---|
| 7 | 586 | 607 | 6.1 | 9.8 | 6.0 |
| 8 | 633 | 650 | 6.0 | 6.9 | 4.1 |
| 9 | 640 | 656 | 6.5 | 4.5 | 2.9 |
| 10a | 661 | 684 | 6.5 | 4.1 | 2.7 |
| 10b | | | | — | — |
| 11b | 667 | NA | 12 | — | — |
| 2 | 515 | 526 | 7.1 | 9.9 | 70 |
| 6 | 553 | 576 | 4.9 | 23.8 | 117 |

Example 7: Cell Studies

Cell Sample Preparation for Fluorescence Imaging

Live cell experiments were performed with HeLa (human), GM07373 (bovine) or S2 (*Drosophila*) cells. HeLa and GM07373 cells were cultured in DMEM medium supplemented with 10% fetal bovine serum, 12.5 mM streptomycin, and 36.5 mM penicillin (Fisher Scientific, Pittsburgh, Pa.) in a 37° C. water jacketed $CO_2$ incubator (Thermo Scientific, Waltham, Mass.). HeLa and GM07373 cells were sub-cultured using 0.25% (w/v) trypsin-EDTA (Life Technology, Carlsbad, Calif.) solution every two days. Cells were sub-cultured onto custom-made glass bottom culture dishes two days before the microscopy experiment. On the day of the microscopy experiment, the growth media was replaced with 20 µM compound 12b in serum-free DMEM for one hour. Cells were rinsed with the imaging medium (pH=7.2, 155 mM NaCl, 5 mM KCl, 2 mM $CaCl_2$, 1 mM $MgCl_2$, 2 mM $NaH_2PO_4$, 10 mM HEPES and 10 mM Glucose) prior to collecting microscopy images. S2 cells were cultured in Shields and Sang M3 insect medium (Sigma-Aldrich, St. Louis, Mo.) with heat-inactivated 10% fetal bovine serum (Irvine Scientific, Santa Ana, Calif.), 12.5 mM streptomycin, and 36.5 mM penicillin in a 22° C. incubator (Fisher Scientific, Pittsburgh, Pa.).[3] S2 cells were incubated with 20 µM of the compound 12b in M3 media for one hour and then washed twice with serum free M3 medium. Incubated S2 cells were allowed to spread on cover glass for half an hour at room temperature, and were then rinsed with BES buffer (pH=7.0) multiple times prior to collecting microscopy images.

Live Cell Fluorescence Imaging

All microscopy experiments were performed on a Nikon Eclipse TE2000U microscope (Melville, N.Y.) operating in wide-field, epi-fluorescence mode and equipped with a 100× Apo, 1.49 numerical aperture oil-immersion objective. HeLa or GM07373 cells were imaged at 36±2° C. in a home-built housing around the microscope. S2 cells were imaged at room temperature. For photolysis, the cells were illuminated with 635±15 nm wavelength light from a mercury lamp (X-Cite 120 PC, EXFO Photonic Solutions Inc., Mississauga, Ontario, Canada) operating at 100% lamp power. Increased fluorescence due to quencher release during the photolysis reaction was collected through excitation (425±45 nm) and emission (605±20 nm) filters from Omega Optical (XF304-1, Brattleboro, Vt.). Fluorescence images were collected every 2 minutes using a PhotonMAX 512 EMCCD camera (Princeton Instruments, Trenton, N.J.) and WinView 2.6 imaging software (Princeton Instruments, Trenton, N.J.). The control experiments were performed without the 635±1.5 nm light illumination. Images were further analyzed with imageJ (National Institute of Health) and IGOR Pro V 6.32A (WaveMetrices Inc., Lake Oswego, Oreg.).

Cytotoxicity Assay

HeLa, GM07373 or S2 cells were incubated with 20 μM of the compound 12b for an hour. Cytotoxicity of the compound was measured using trypan blue exclusion assays. Equal volumes of the cell suspension and 0.4% trypan blue stain (Thermo Scientific™ Hyclone™ Trypan Blue, Waltham, Mass.) were incubated for 3 minutes at room temperature. The number of viable cells that excluded the dye was counted using a hemacytometer (Hausser Bright-Line, Hausser scientific, Horsham, Pa.) and an optical microscope.

TABLE 3

Cytotoxicity of compounds as measured with trypan blue exclusion assay

| | % of Viable cells |
|---|---|
| HeLa cells | |
| No treatment | 90 ± 3 |
| Cells incubated with 20 μM compound 12b | 92 ± 5 |
| S2 cells | |
| No treatment | 95 ± 2 |
| Cells incubated with 20 μM compound 12b | 93 ± 2 |
| GM07373 cells | |
| No treatment | 90 ± 1 |
| Cells incubated with 20 μM compound 12b | 92 ± 5 |

Uncertainty represents standard deviation from two measurements

What is claimed is:

1. A method for photoreleasing a moiety G, or a fragment thereof, from a compound of formula A-G comprising:
   irradiating a composition comprising the compound of formula A-G at a wavelength of >500 nm, so as to photorelease the moiety G, or a fragment thereof, from the moiety A;
   wherein:
   the moiety A is a moiety of formula I:

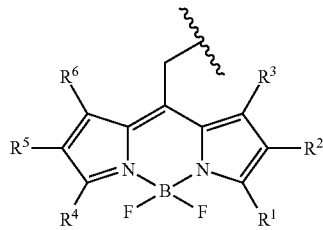

I wherein:
the wavy line represents the attachment point of the moiety A to the moiety G or L-G;
$R^1$, $R^2$, $R^3$, $R^4$, $R^5$, and $R^6$ are each, independently, hydrogen, halogen, optionally substituted $C_1$-$C_6$-alkyl, optionally substituted $C_2$-$C_6$-alkenyl or ($C_6$-$C_{14}$-aryl)-($C_2$-$C_6$-alkenyl-), wherein the ($C_6$-$C_{14}$-aryl)-($C_2$-$C_6$-alkenyl-) is optionally substituted on the $C_2$-$C_6$-alkenyl or the $C_6$-$C_{14}$-aryl; and
the moiety G is a protein, an oligopeptide, an amino acid, an oligonucleotide, an ion, or a small molecule.

2. The method of claim 1, wherein the compound of the formula A-G has a wavelength absorption maximum, $\lambda_{max}$, between about 510 nm to about 1000 nm.

3. The method of claim 1, wherein the compound of the formula A-G has an extinction coefficient measured at the compound A-G $\lambda_{max}$, of from about $4.0 \times 10^4$ $M^{-1}$ $cm^{-1}$ to about $8.0 \times 10^4$ $M^{-1}$ $cm^{-1}$.

4. The method of claim 1, wherein the protein comprised in the moiety G is selected from the group consisting of caspases, phosphatases, cholinesterases, esterases, transferases, restriction endonucleases, and hemoglobin.

5. The method of claim 1, wherein the small molecule comprised in the moiety G is at least one of a dye, fragrance, nucleoside, nucleotide, neurotransmitter, and pharmaceutical agent.

6. The method of claim 5, wherein the nucleoside comprised in the moiety G is adenine, thymidine, cytosine, guanosine or uridine.

7. The method of claim 5, wherein the nucleotide comprised in the moiety G is adenosine triphosphate (ATP) or guanosine triphosphate (GTP).

8. The method of claim 5, wherein the neurotransmitter comprised in the moiety G is norepinephrine, glutamate, dopamine, gamma-aminobutyric acid, serotonin or an endorphin.

9. The method of claim 1, wherein $R^1$ and $R^4$ are each, independently, an optionally substituted $C_1$-$C_6$-alkyl.

10. The method of claim 1, wherein $R^1$ and $R^4$ are each methyl.

11. The method of claim 9, wherein $R^3$ and $R^6$ are each, independently, an optionally substituted $C_1$-$C_6$-alkyl.

12. The method of claim 11, wherein $R^3$ and $R^6$ are each methyl.

13. The method of claim 11, wherein $R^2$ and $R^5$ are each, independently, an optionally substituted $C_1$-$C_6$-alkyl.

14. The method of claim 13, wherein $R^2$ and $R^5$ are each, independently, methyl or ethyl.

15. The method of claim 13, wherein $R^2$ and $R^5$ are each, independently, halogen.

16. The method of claim 1, wherein $R^1$ and $R^4$ are each, independently, ($C_6$-$C_{14}$-aryl)-($C_2$-$C_6$-alkenyl-), wherein the ($C_6$-$C_{14}$-aryl)-($C_2$-$C_6$-alkenyl-) is optionally substituted on the $C_2$-$C_6$-alkenyl or the $C_6$-$C_{14}$-aryl.

17. The method of claim 16, wherein $R^1$ and $R^4$ are each, independently, ($C_6$-$C_{10}$-aryl)-($C_2$-$C_4$-alkenyl-), wherein the ($C_6$-$C_{10}$-aryl)-($C_2$-$C_4$-alkenyl-) is optionally substituted on the $C_2$-$C_4$-alkenyl or the $C_6$-$C_{10}$-aryl.

18. The method of claim 1, wherein the moiety A is a moiety of the formula:

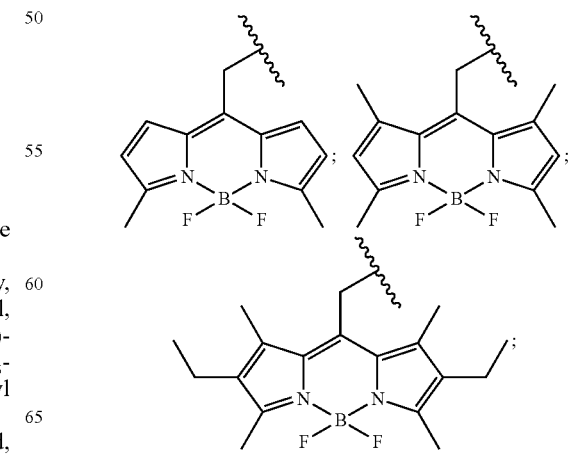

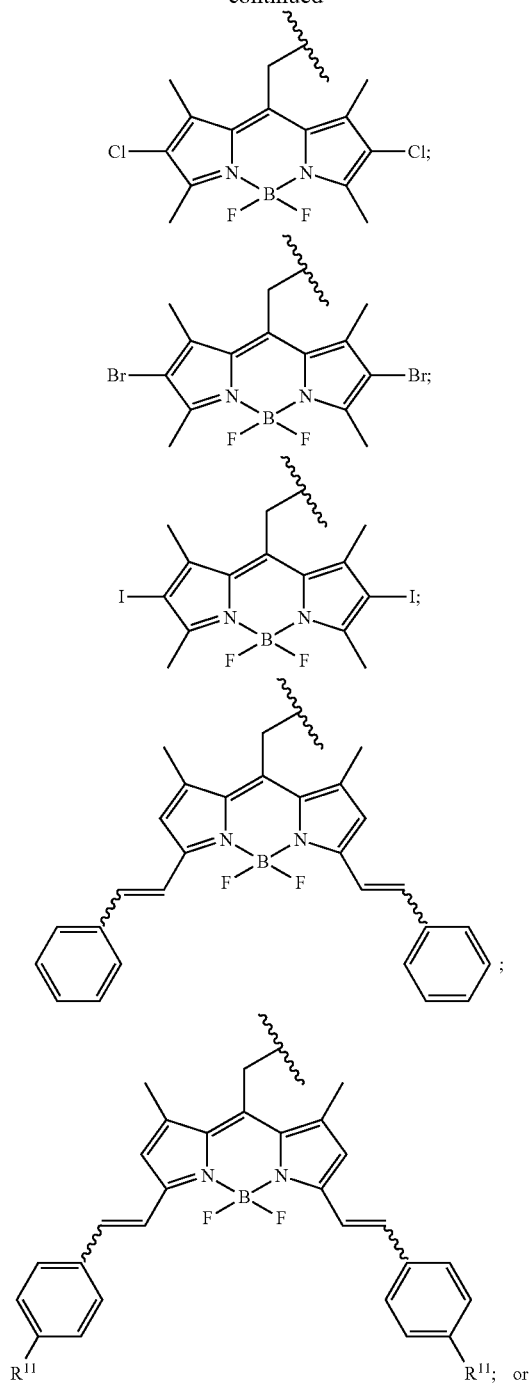

wherein $R^{11}$ is H; $C_{1-6}$-alkyl-O—; —N($R^8$)$_2$, wherein each $R^8$ is hydrogen, alkyl, aryl or alkaryl, or —O—$C_{1-6}$-alkyl-O—$C_{1-6}$-alkyl.

19. The method of claim 18, wherein $R^{11}$ is H; —OCH$_3$, —N(CH$_3$)$_2$; or —(OCH$_2$CH$_2$)$_3$OCH$_3$).

20. The method of claim 18, wherein the moiety A is a moiety of the formula:

21. The method of claim 1, wherein the moiety G is a moiety of the formula —O-G', wherein G' is at least one of a protein, an oligonucleotide, a polynucleotide, an ion, and a small molecule.

* * * * *